(12) United States Patent
Peterman et al.

(10) Patent No.: US 12,370,056 B2
(45) Date of Patent: Jul. 29, 2025

(54) DEVICES AND METHODS FOR ALTERING SPINAL LATERAL CURVATURE

(71) Applicant: 3SPINE, INC, Chattanooga, TN (US)

(72) Inventors: Marc M Peterman, Duxbury, MA (US); Steven C Humphreys, Chattanooga, TN (US); Scott Hodges, Soldatna, AK (US)

(73) Assignee: 3SPINE, Inc., Chattanooga, TN (US)

( * ) Notice: Subject to any disclaimer, the term of this patent is extended or adjusted under 35 U.S.C. 154(b) by 184 days.

(21) Appl. No.: 18/229,149

(22) Filed: Aug. 1, 2023

(65) Prior Publication Data

US 2024/0024122 A1 Jan. 25, 2024

Related U.S. Application Data

(63) Continuation of application No. 17/313,435, filed on May 6, 2021, which is a continuation of application (Continued)

(51) Int. Cl.
*A61F 2/44* (2006.01)
*A61B 17/064* (2006.01)
(Continued)

(52) U.S. Cl.
CPC .......... *A61F 2/442* (2013.01); *A61B 17/0642* (2013.01); *A61B 17/068* (2013.01); *A61B 17/70* (2013.01); *A61B 17/7064* (2013.01); *A61F 2/4405* (2013.01); *A61F 2/4425* (2013.01); *A61F 2/4455* (2013.01); *A61F 2/4611* (2013.01); *A61B 2017/0648* (2013.01); *A61B 17/7001* (2013.01); *A61F 2002/30331* (2013.01); *A61F 2002/30507* (2013.01); *A61F 2002/30517* (2013.01); *A61F 2002/30525* (2013.01); *A61F 2002/30563* (2013.01); *A61F 2002/30578* (2013.01); *A61F 2002/30579* (2013.01); *A61F 2002/30624* (2013.01); *A61F 2002/30652* (2013.01); *A61F 2002/30654* (2013.01); *A61F 2002/30662* (2013.01); *A61F 2002/30828* (2013.01); *A61F 2002/30841* (2013.01); *A61F 2002/30884* (2013.01); *A61F 2002/30904* (2013.01); *A61F 2002/448* (2013.01); *A61F 2002/4627* (2013.01); *A61F 2002/4628* (2013.01); *A61F 2220/0025* (2013.01); *A61F 2220/0033* (2013.01);
(Continued)

(58) Field of Classification Search
CPC .......... A61F 2/44; A61F 2/442; A61F 2/4405; A61F 2/4425; A61F 2002/443; A61B 2017/564
See application file for complete search history.

(56) References Cited

U.S. PATENT DOCUMENTS 7,785,351 B2 * 8/2010 Gordon ................. A61F 2/4405
606/259
8,603,168 B2 * 12/2013 Gordon .............. A61B 17/7023
606/260
(Continued)

*Primary Examiner* — Ellen C Hammond
(74) *Attorney, Agent, or Firm* — BRAINSPARK ASSOCIATES, LLC

(57) ABSTRACT

Disclosed are systems, devices, methods and surgical procedures for altering and/or correcting the alignment of adjacent bones, including bones of the spine.

20 Claims, 30 Drawing Sheets

Related U.S. Application Data

No. PCT/US2019/060800, filed on Nov. 11, 2019, application No. 18/229,149 is a continuation-in-part of application No. 17/023,864, filed on Sep. 17, 2020, now Pat. No. 11,890,202, which is a continuation of application No. 15/955,611, filed on Apr. 17, 2018, now Pat. No. 10,821,003.

(60) Provisional application No. 62/758,062, filed on Nov. 9, 2018, provisional application No. 62/654,963, filed on Apr. 9, 2018, provisional application No. 62/486,329, filed on Apr. 17, 2017.

(51) Int. Cl.
*A61B 17/068* (2006.01)
*A61B 17/70* (2006.01)
*A61F 2/46* (2006.01)
*A61F 2/30* (2006.01)

(52) U.S. Cl.
CPC ............. *A61F 2250/0004* (2013.01); *A61F 2310/00023* (2013.01); *A61F 2310/00029* (2013.01); *A61F 2310/00796* (2013.01); *A61F 2310/00976* (2013.01)

(56) References Cited

U.S. PATENT DOCUMENTS

| | | | |
|---|---|---|---|
| 2002/0068941 A1* | 6/2002 | Hanson | A61F 2/4611 606/79 |
| 2006/0247654 A1* | 11/2006 | Berry | A61B 17/1757 606/96 |
| 2007/0123884 A1* | 5/2007 | Abdou | A61B 17/8033 606/279 |

* cited by examiner

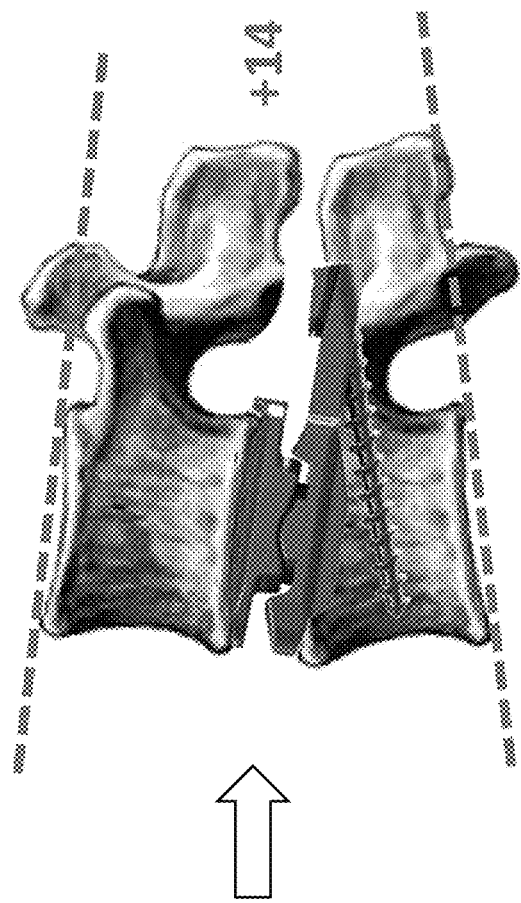
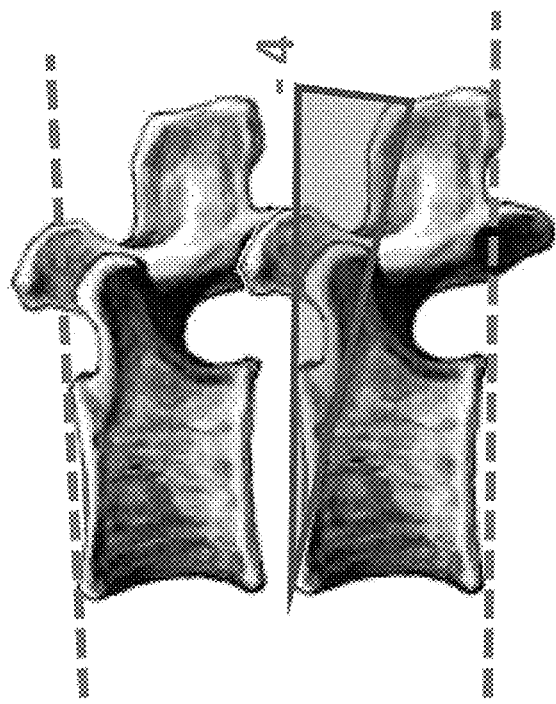
FIG. 4D

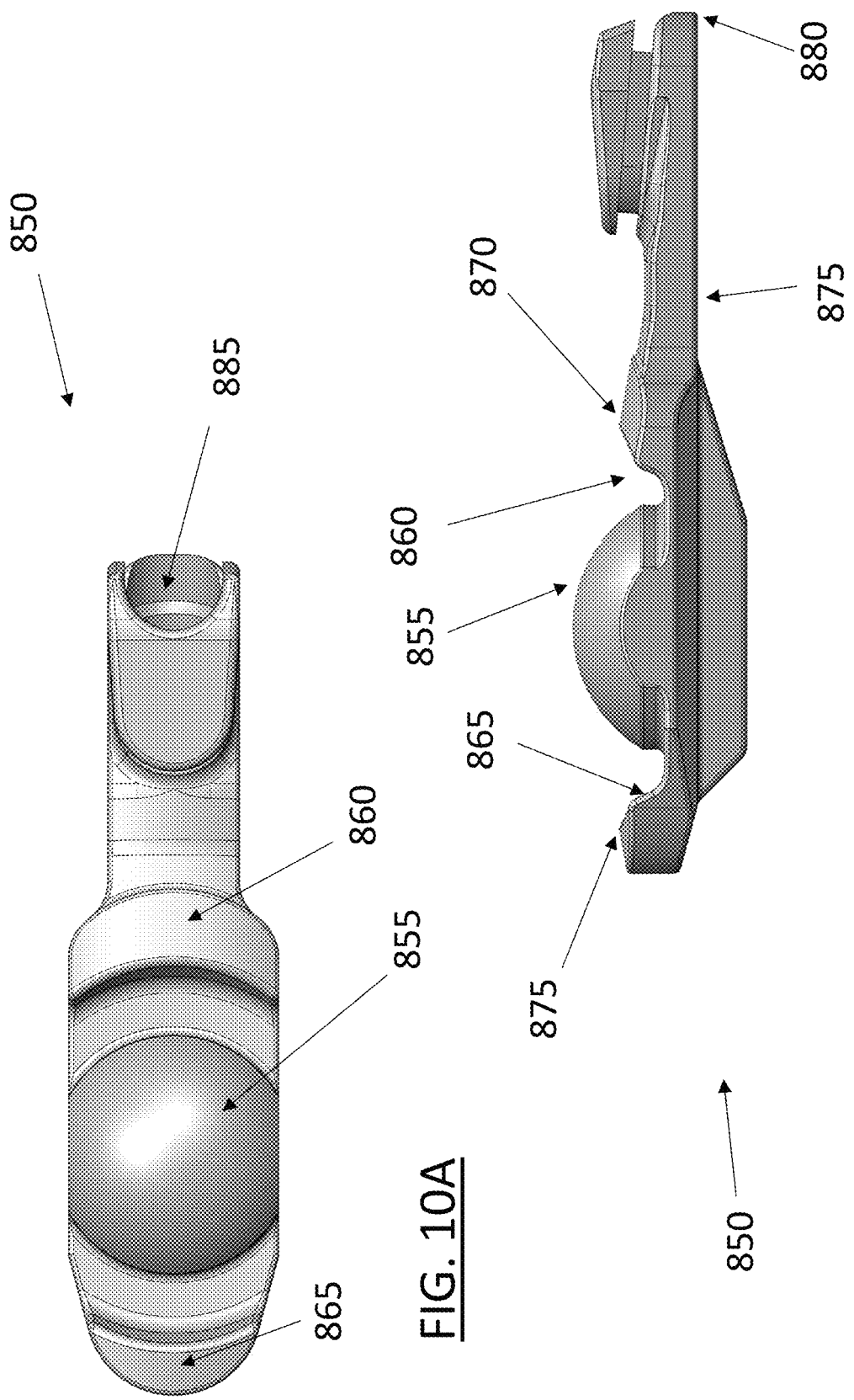

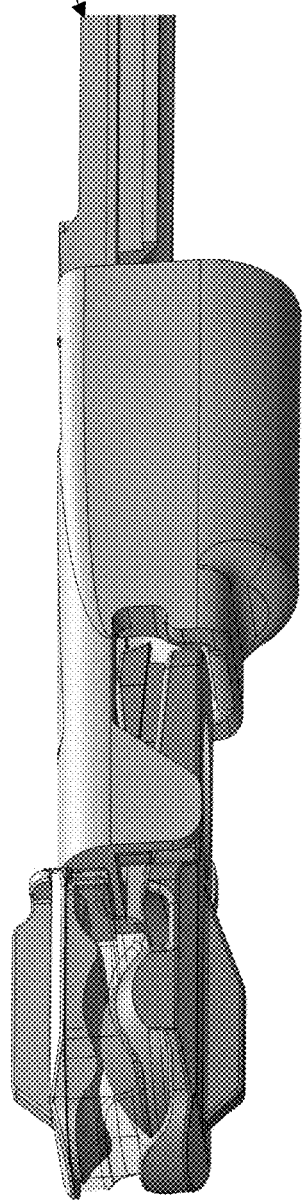
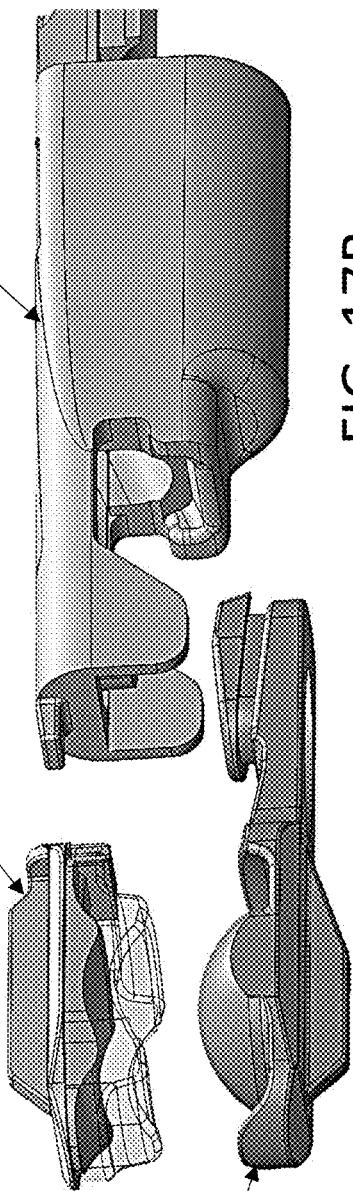
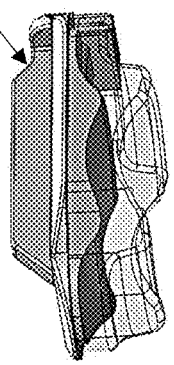
FIG. 17A
FIG. 17B

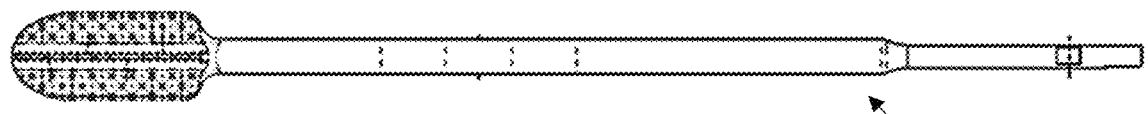
FIG. 21A    2100
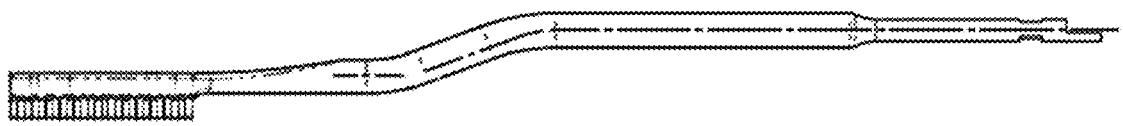
FIG. 21B
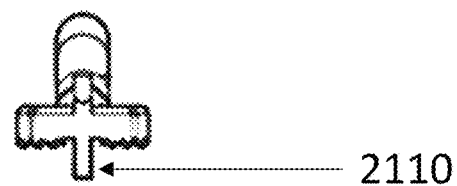
2110
FIG. 21C

DEVICES AND METHODS FOR ALTERING SPINAL LATERAL CURVATURE

CROSS-REFERENCE TO RELATED APPLICATIONS

This application is a continuation of U.S. patent application Ser. No. 17/313,435 entitled "INTERVERTEBRAL SPINAL IMPLANT AND SURGICAL METHODS," filed May 6, 2011, which is a continuation of Patent Cooperation Treaty Patent Application PCT/US19/60800 entitled "INTERVERTEBRAL SPINAL IMPLANT AND SURGICAL METHODS," filed Nov. 11, 2019, which in turn claims the benefit of U.S. Provisional Patent Application Ser. No. 62/758,062 entitled "METALLIC AND NON-METALLIC BEARING COUPLES FOR SPINAL IMPLANTS," filed Nov. 9, 2018, the disclosures of which are each incorporated by reference herein in their entireties.

This application is also a continuation-in-part of U.S. patent application Ser. No. 17/023,864 entitled "SPINAL OSTEOTOMY," filed Sep. 17, 2020, which is a continuation of U.S. patent application Ser. No. 15/955,611 entitled "SPINAL OSTEOTOMY," filed Apr. 17, 2018, which issued on Nov. 3, 2020 as U.S. Pat. No. 10,821,003, which in turn claims the benefit of and priority to U.S. Provisional Patent Application Ser. No. 62/654,963 entitled "Spinal Osteotomy," filed Apr. 9, 2018, and U.S. Provisional Patent Application Ser. No. 62/486,329 entitled "HHALL Osteotomy," filed Apr. 17, 2017. The disclosures of each of these references are incorporated by reference herein in their entireties.

TECHNICAL FIELD

The present invention relates generally to devices, methods, systems and techniques for repairing and/or stabilizing the spine and/or other bones of a patient during spinal surgery.

BACKGROUND

At times, the source of a patients back pain may not be clear. Among possible causes for such pain are disease, degradation and/or injury to the spinal bones and/or discs of the spine, as well as to various ancillary structures such as the lamina and/or associated facet joints. While spinal fusion and/or disc arthroplasty procedures have been successful in treating spinal joints to reduce pain, such treatments are often limited in their efficacy, often fuse or immobilize portions or a patient's spine, and are often unable to address and/or correct severe spinal deformities, including spinal dislocations and/or curvature abnormalities such as juvenile and/or adult scoliosis. Therefore, a motion preserving joint replacement system is needed that can reduce and/or correct severe spinal deformities while replacing all or part of the function of the spinal disc and/or associated spinal structures.

SUMMARY OF THE INVENTION

In various embodiments, surgical methods and techniques are described wherein portions of a patient's spinal bones may be shaped, shaved, resected and/or removed, including portions of a vertebral endplate and/or pedicular portion(s) (and/or associated structures), with at least one or more portions of the pedicle being retained to provide at least partial support for a prosthetic system that is implanted between the upper and lower vertebrae.

In various embodiments, the prosthetic system can comprise a pair of independent joint components, each of the independent joint component pairs comprising an upper joint component and a lower joint component. The upper joint component can comprise an upper contact surface and an upper articulation surface, and the lower joint component can comprise a lower contact surface and a lower articulation surface configured to movably engage the upper articulation surface to form an articulating joint pair, with two articulating joint pairs implanted into an intervertebral space between adjacent vertebrae to form an articulating joint. The articulating joint is adapted for implantation within a disc space between the upper and lower vertebrae, allowing the upper and lower vertebrae to move relative to one another. The lower joint components will also each desirably include supports or bridge components extending posteriorly from the disc space, with at least a portion of each bridge component including an outer surface which abuts and/or engages with at least a portion of a pedicle and/or portions of the vertebral arch of the lower vertebral body.

In various embodiments, the individual components of the articulating joint, specifically the various upper and lower joint components of the two articulating joint pairs, are configured such that these components can assume a variety of differing positions and/or orientations (i.e., relative to each other and/or relative to the vertebral bodies in which they are implanted) while maintaining a capacity to articulate in a desired manner. Such design features allow the use of similar and/or identical joint components at all levels of the spine, even if patient injuries and/or anatomical constraints require modification of component positioned at differing levels of the spine.

In still another embodiment, a surgical method comprises non-invasively imaging at least upper and lower vertebral bodies of a patient's spine, and then preoperatively planning the surgical removal of some portions of an endplate and one or more pedicles of the lower vertebral body to alter, restore and/or correct the alignment between the upper and lower vertebral bodies to a desired and/or more anatomically correct alignment. Surgical removal according to the preoperative plan can be accomplished, which can include removal of the endplate and/or a portion of one or more pedicles of the lower vertebral body, and then insertion of a prosthetic system between the upper and lower vertebrae, wherein the system comprises an upper joint component and a lower joint component, with the lower joint component including a support extending posteriorly from the lower joint component, the posterior support including a surface adapted and configured to fit within at least a remaining portion of one or more pedicles of the lower vertebral body.

In the various embodiments described herein the planning and surgical corrections to the spinal alignment can include alterations to the lordotic curvature of the patient's spine, alterations to the lateral curvature of the patient's spine (i.e., to address scoliosis, for example), and/or various combinations thereof. If desired, a surgical correction to a specific region of the spine may result in a more-normal anatomical alignment of the affected segment, or the surgical correction may result in an alignment that is further away from the natural alignment (such as where the treated segment desirably compensates for other misaligned levels that may not be surgically treated). In various embodiments, the anatomical imaging, analysis, approach, vertebral preparation, implant preparation and/or placement can be accomplished with the aid of surgical navigation and/or robotic guidance.

Due to the complex nature of the preoperative planning and/or execution, these tools may be particularly well suited for the present invention to allow execution of the plan in the operative environment.

BRIEF DESCRIPTION OF THE DRAWINGS

The foregoing and other objects, aspects, uses, features, and advantages of embodiments will become more apparent and may be better understood by referring to the following detailed description of the preferred embodiments, taken in conjunction with the accompanying drawings, wherein:

FIGS. 4A through 4D depicts exemplary planning steps for altering and/or correcting the lordotic alignment of a functional spinal unit;

FIGS. 10A and 10B depict top and side plan views of an exemplary embodiment of a lower component assembly;

FIGS. 17A and 17B depict partial enlarged and exploded views of a distal tip of an insertion tool with an upper component and a lower component secured thereupon; and FIGS. 18A through 21C depict exemplary surgical rasps or tools for preparing vertebral anatomy.

DETAILED DESCRIPTION

Figure 1:
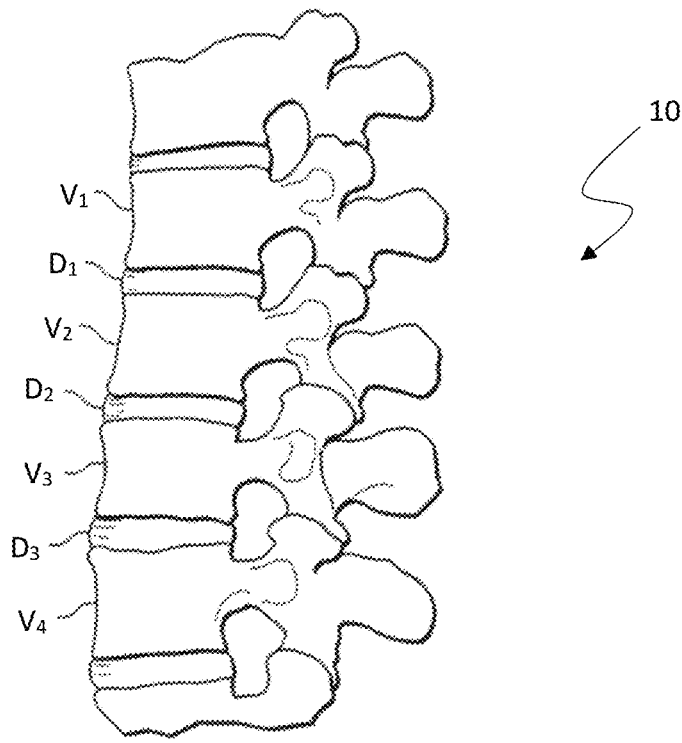
FIG. 1 depicts a sagittal view of the lumbar spinal region of a healthy, human spinal column.

Various features of the present invention include the recognition of a need for a more effective and versatile system of addressing spinal disease and deformities, including the correction and/or alteration of spinal levels using a motion preserving construct. A variety of configurations, sizes and shapes of such components and associated tools can be utilized in diverse anatomical regions, including use in spinal surgery as well as other anatomical locations. In various medical applications, the disclosed components and related surgical tools and techniques can desirably facilitate the treatment of various types of bone disease and/or damage by surgeons, which can be important to achieve the most accurate and best implant performance and/or fit, as well as facilitate patient recovery.

This specification describes novel systems, devices and methods to treat spinal fractures. Aspects of the present invention will be described with regard to the treatment of vertebral bodies at the lumbar and/or thoracic levels. It should be appreciated, however, that various aspects of the present invention may not limited in their application to thoracic or lumbar injuries. The systems and methods may be applicable to the treatment of fractures in diverse bone types. Embodiments will now be described with reference to the drawings, wherein like reference numerals are used to refer to like elements throughout. It should be understood that the figures are not necessarily to scale.

The present disclosure relates generally to systems and methods for spinal surgery and, more particularly in some embodiments, to spinal arthroplasty systems and methods for posterior implantation. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Various embodiments disclosed herein can be utilized in conjunction with various devices, tools and/or surgical techniques described in co-pending U.S. patent application Ser. No. 15/955,611, filed Apr. 17, 2018 and entitled "Spinal Osteotomy," the disclosure of which is incorporated herein by reference in its entirety.

Referring first to FIG. 1, a sagittal view of a vertebral column 10 is shown, illustrating a sequence of vertebrae V1, V2, V3, V4 separated by natural intervertebral discs D1, D2, D3, respectively. Although the illustration generally depicts a lumbar section of a spinal column, it is understood that the devices, systems, and methods of this disclosure may also be applied to all regions of the vertebral column, including thoracic and cervical regions.

Figure 2:
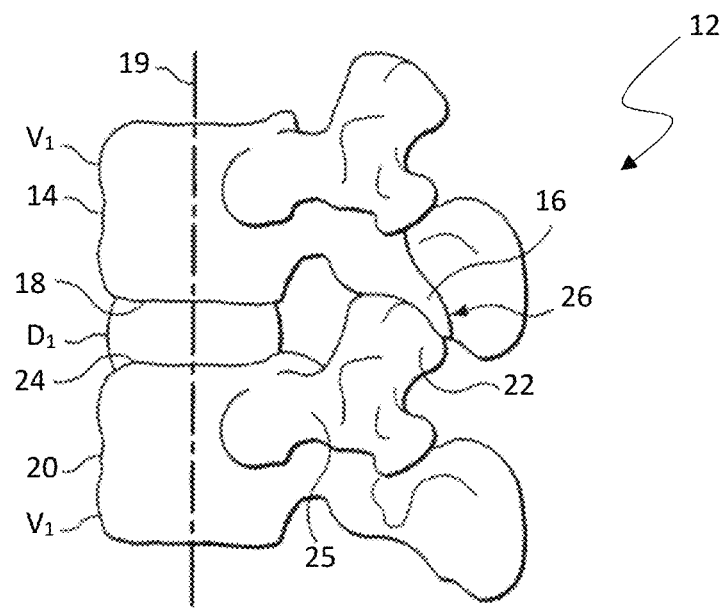
FIG. 2 depicts a sagittal view of a single spinal joint.

Referring now to FIG. 2, a vertebral joint 12 of the vertebral column 10 includes the adjacent vertebrae V1, V2 between which the intervertebral disc D1 extends. The vertebra V1 includes a generally cylindrical vertebral body portion 14, an inferior articular process 16, and an inferior endplate 18. The vertebra V2 includes a generally cylindrical vertebral body portion 20, a superior articular process 22, and a superior endplate 24. For reference purposes, a longitudinal axis 19 extends through the centers of the cylindrical vertebral body portions 14, 20. A pedicle 25 extends between the vertebral body portion 20 and superior articular process 22. The inferior articular process 16 and the superior articular process 22 form a facet or zygapophyseal joint 26. The facet joint 26 has a fluid filled capsule and cartilage to provide articulating surfaces for the articular processes 16, 22. Both the disc D1 and the facet joint 26 permit motion between adjacent bone surfaces, allowing the total vertebral joint 12 a normal range of flexion/extension, lateral bending, and rotational motion. As the disc D1 and/or the facet joint 26 deteriorate due to aging, injury, disease, or other factors, all or portions of the disc, the facet joint, and/or the articular processes 16, 22 may be removed and replaced by a prosthetic device which may preserve motion in the spinal joint 12. Although not described in detail, a second bilateral prosthetic device may also be used to replace a portion of the function of disc D1 and/or the function of a second facet joint opposite the facet joint 26.

Figure 3A:
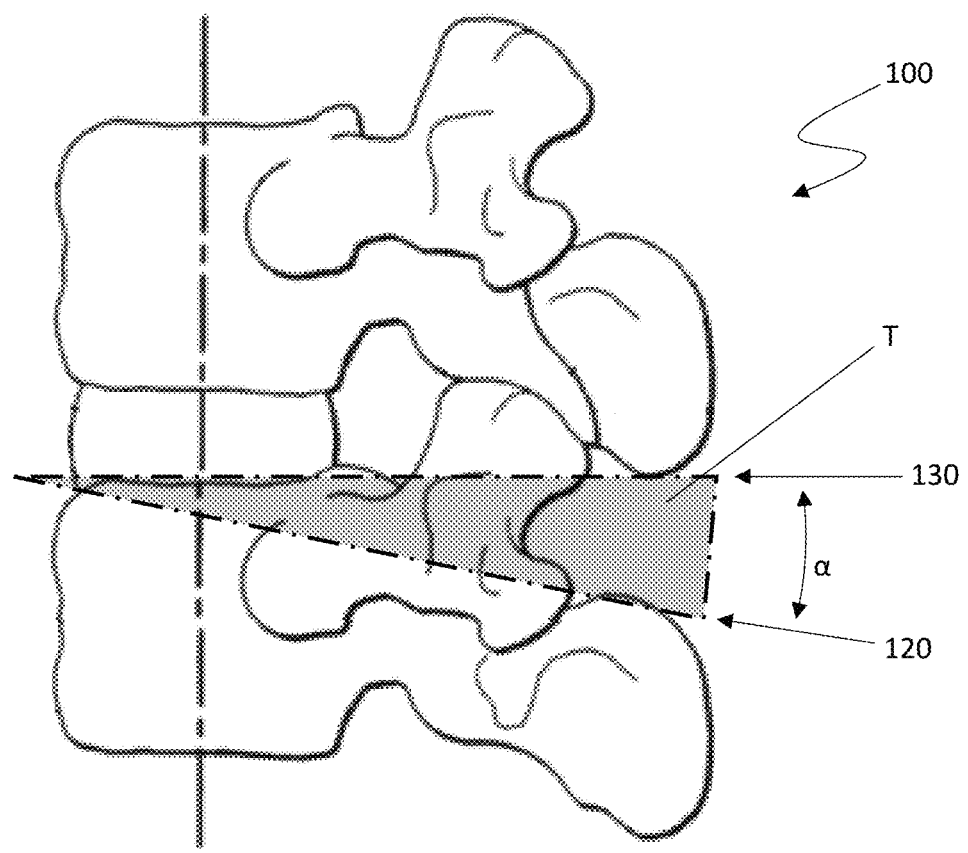
FIG. 3A is lateral view of one exemplary embodiment of a surgical technique for altering the alignment of a functional spinal unit.

FIG. 3A depicts a side view of one exemplary spinal motion unit 100 that is undergoing a surgical procedure in accordance with one exemplary embodiment of the present invention. In this embodiment, preoperative image data of the spinal motion unit has been obtained, and a surgical plan to alter the alignment of the spinal motion has being proposed. In this embodiment, a proposed lower component alignment path 120 has been presented, which will desirably result in the surgical removal of a "wedge" of bony material from the lower vertebral body 105 and/or one or both pedicles 110, which is represented by the shaded triangle "T" of FIG. 3A (involving removal of bony material at or below the anatomical alignment line 130 up to the revised alignment line of 120). Desirably, this surgical plan will allow some and/or all of at least the bottom of the pedicles to be preserved during such removal, such that the remaining portions of the pedicle are attached to the vertebral body, to provide additional stability to lower surfaces of the implant. If desired, the resection may be symmetrical on each side of the vertebral body, or the resection may be asymmetrical in some fashion.

Because of various anatomical differences between vertebral levels, some vertebral levels will typically accommodate a greater degree of osteotomy correction than others. For example, at the L1/L2 level, an osteotomy angle α of up to 10 degrees (i.e., a correction of from zero to 10 degrees) can be accomplished on one or both sides of a treated lower vertebral body, while retaining sufficient pedicular structure underneath the implant to maintain adequate implant support. At the L2/L3 level, an osteotomy angle α of up to 15 degrees (i.e., a correction of from zero to 15 degrees) can be accomplished on one or both sides of a treated lower vertebral body, while retaining sufficient pedicular structure underneath the implant to maintain adequate implant support. At the L3/L4 level, an osteotomy angle α of up to 20 degrees (i.e., a correction of from zero to 20 degrees) can be accomplished on one or both sides of a treated lower vertebral body, while retaining sufficient pedicular structure underneath the implant to maintain adequate implant support. At the L4/L5 level, an osteotomy angle α of up to 25 degrees (i.e., a correction of from zero to 25 degrees) can be accomplished on one or both sides of a treated lower vertebral body, while retaining sufficient pedicular structure underneath the implant to maintain adequate implant support. At the L5/S1 level, an osteotomy angle α of up to 30 degrees (i.e., a correction of from zero to 30 degrees) can be accomplished on one or both sides of a treated lower vertebral body, while retaining sufficient pedicular structure underneath the implant to maintain adequate implant support. Such a significant degree of surgical correction in a procedure utilizing a motion preserving implant is heretofore unheard of in spinal surgery, and such dramatic corrections are even infrequent using fusion implants and/or during other corrective surgeries.

In various embodiments, the use of robotics and/or computer guided surgical platforms (and/or computer-aided navigation) are contemplated herein, including in the planning and/or execution stages of the surgery.

Figure 3B:
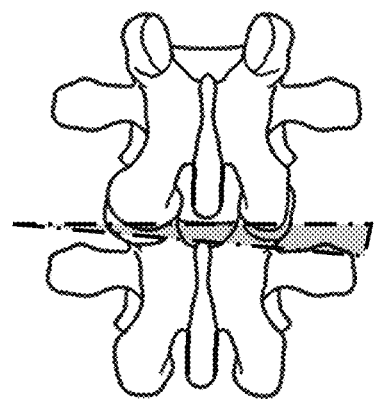
FIG. 3B is a posterior view of another exemplary embodiment of a surgical technique for altering the alignment of a functional spinal unit.

FIG. 3B depicts a posterior view of the exemplary spinal motion unit 100, where an asymmetrical resection is being planned to desirably correct an undesirable medial/lateral curvature of the spine. In this embodiment, more material will be resected from right side of the spinal motion unit than from the left side, which will desirably induce a slight medial curvature to the patient's spine (i.e., providing a desired coronal plan correction). In addition, as previously noted, the surgical plan will desirably allow some and/or all of at least the bottom of the pedicles to be preserved during such removal, such that the remaining portions of the pedicle are attached to the vertebral body, to provide additional stability to lower surfaces of the implant.

Figure 3C:
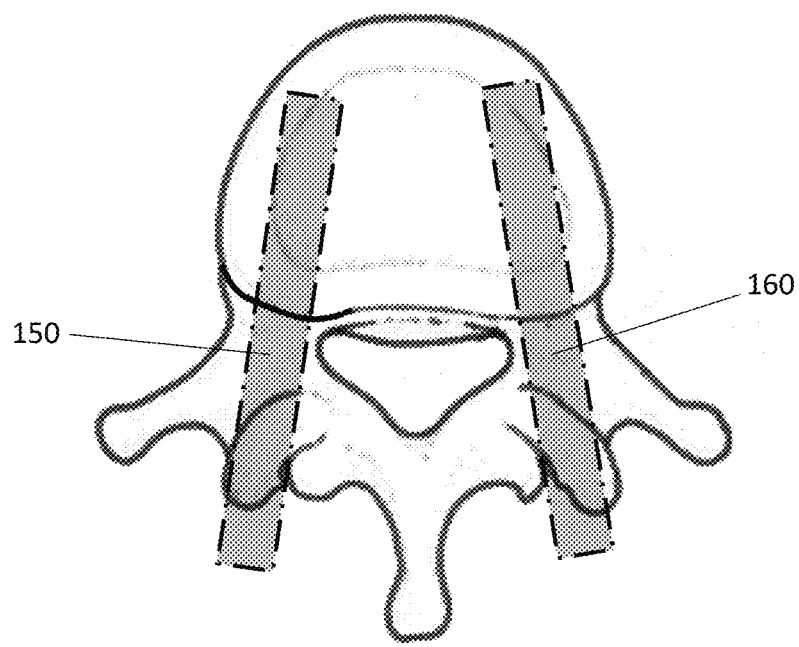
FIG. 3C is a superior view of a surgical technique for altering the alignment of a functional spinal unit.

FIG. 3C depicts a top view of a vertebral body of the surgical plan on FIG. 3A, in which the proposed bone "wedges" are shown in shadow as planning boxes 150 and 160. In this embodiment, the wedges could be taken from both sides for sagittal correction, or both side asymmetrically or unilaterally for combined coronal and sagittal correction.

Figure 4A:
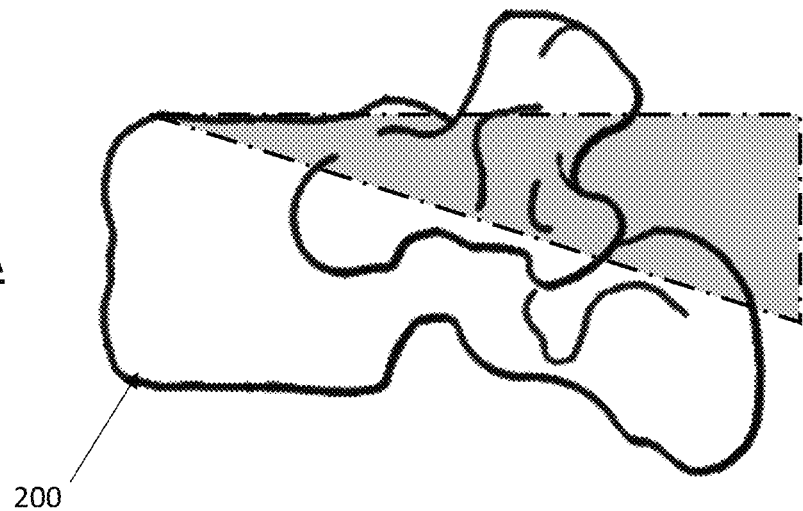
Figure 4B:
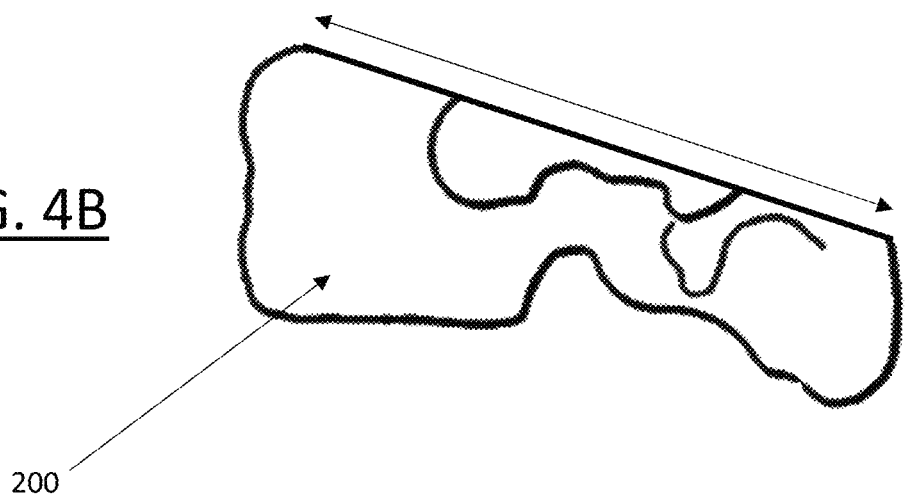
Figure 4C:
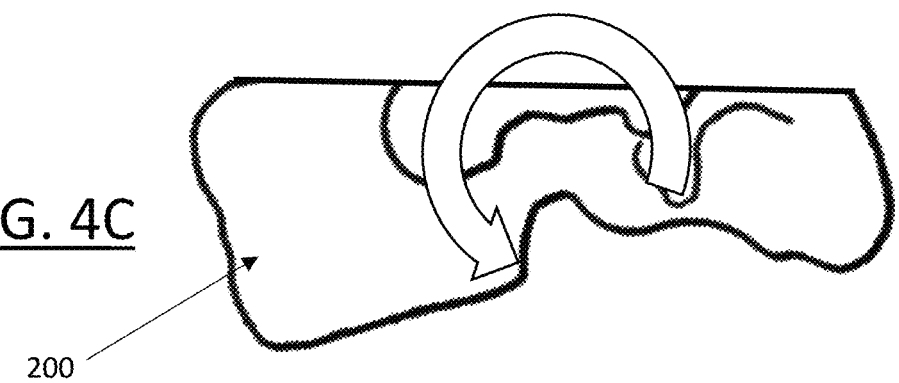

FIGS. 4A through 4D depict one exemplary lordotic correction that could be obtained using the teachings of the present invention. In this embodiment, a vertebral body 200 is imaged, and a surgical resection plan is proposed (indicated as the shaded triangle). FIG. 4B shows the vertebral body 200 after resection, and FIG. 4C depicts the new orientation of the vertebral body 200 after resection is complete, which could represent an increased lordotic curvature of the lumbar spine when accomplished at the lumbar level. FIG. 4D depicts the resulting correction to the functional spinal unit, wherein a negative 4 degree curvature was altered and stabilized to a positive 14 degree curvature using the techniques and implants described herein. In various embodiments, a surgical correction can also address medial/lateral correction, such as where one side of a vertebral body (i.e., the left side) is altered to a different degree than the opposite side (i.e., right side) of a single vertebral body. In such a case, the curvature of the spine may be altered to the left or right side of the patient, which may have particular utility in correcting scoliotic curvature and/or the like.

In preparing the vertebral body of FIG. 4A, it is contemplated that a power reciprocating tool, rasp or similar surgical tool or drill can be utilized to prepare at least the lower vertebral surface, such as the rasps depicted in FIGS. 18A through 21C. In this embodiment, a rasp may be introduced into the surgical field, with a forward portion of the rasp located on the endplate of the lower vertebral body, near an anterior portion of the vertebral body, and when actuated the rasp can be pushed downward into the vertebral body along a curving path, which desirably provides increased pressure on a posterior section of the rasp—which cuts the posterior vertebral body more quickly and/or aggressively than the anterior portion of the endplate or vertebral body, desirably creating a wedge or channel extending through the posterior vertebral body and/or pedicle. Depending upon the desired depth and/or angle of cut, the rasp may be utilized to cut completely through the cortical bone of the upper endplate and/or posterior cortical ring of the vertebral body, including portions of the pedicle, which may be accomplished with and/or without complete removal of the cortical bone on an anterior portion of the treated endplate.

Figure 5:
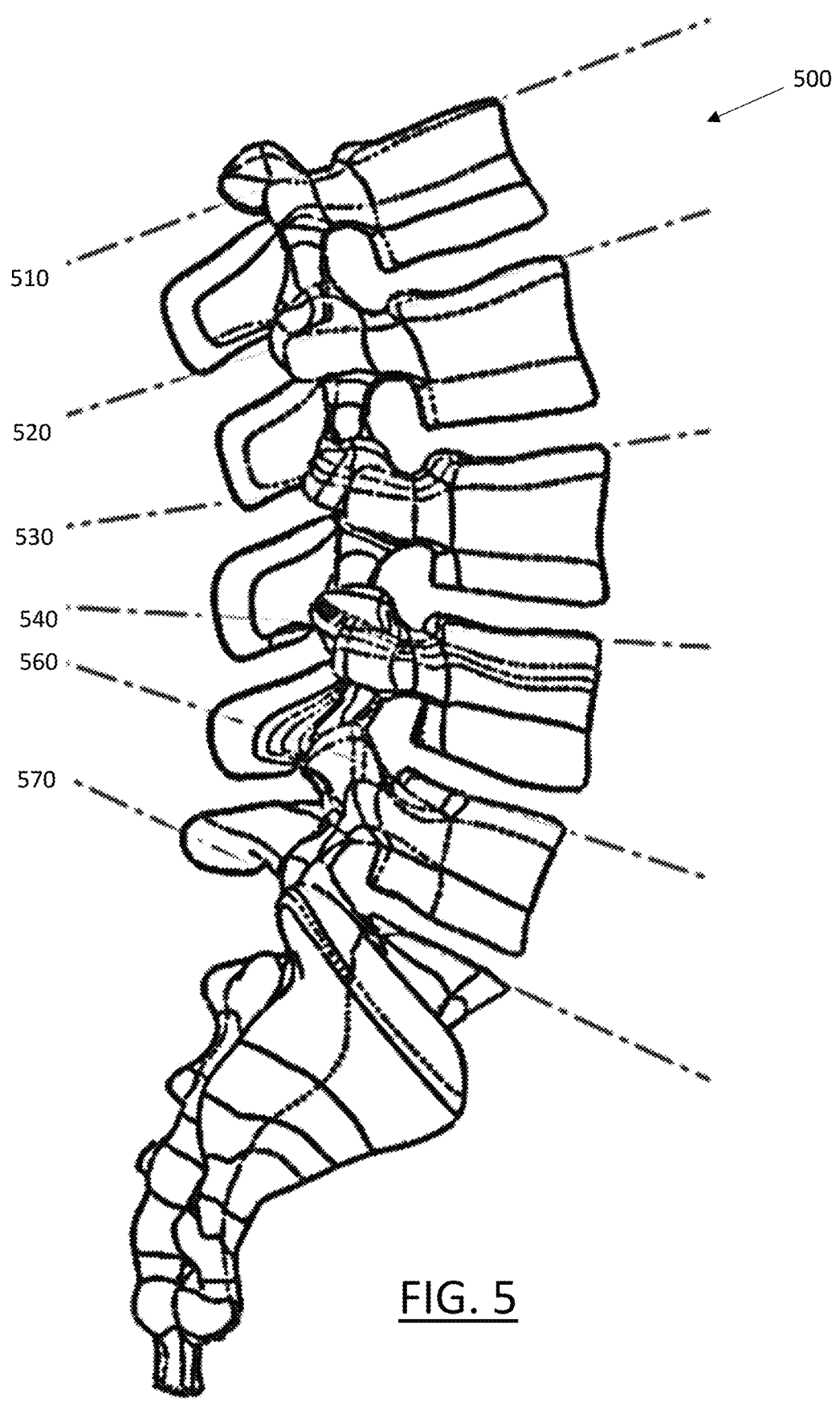
FIG. 5 depicts a lateral view of an exemplary lower spinal segment, with lumbar lordotic angular variance across various spinal levels indicated by dotted lines.

FIG. 5 depicts a lateral view of an exemplary lower spinal segment 500, with typical lumbar lordotic angular variance across various spinal levels indicated by dotted lines. In general, a surgical procedure to repair a particular vertebral level will often seek to approximate the relevant lordotic angles depicted herein, although normal anatomical variance across a normal patient population may cause a surgeon to alter these angles somewhat in their surgical repair. In addition, where a pre-existing injury has significantly altered the dynamics and/or kinematics of a patient's spine, a surgeon may opt for surgical repairs that attempt to restore and/or approximate the overall natural lordotic curvature of the patient's spine, even where such correction might alter a single level or group of levels to less desirable and/or non-desirable angles (i.e., in an attempt to restore a more natural anatomical curvature to the spine as a whole). For example, as discussed in "Lumbar lordosis: a study of angle values and of vertebral bodies and intervertebral discs role" By Fonseca Damasceno et al, published in Acta Orthopedica Brasileira, (ISSN 1809-4406), as compared to the sacral angle 570, L1 normally has a typical angular range of 14 degrees to −9 degrees (510: 14°:−9°), L2 has a typical angular range of 7 degrees to −8 degrees (520: 7°:−8°), L3 has a typical angular range of 14 degrees to −9 degrees (530: 14°/−9°), L4 has a typical angular range of 4 degrees to −14 degrees (540: 4°:−14° and L5 has a typical angular range of 0 degrees to −19 degrees (550: 0°:−19°).

Figure 6A:
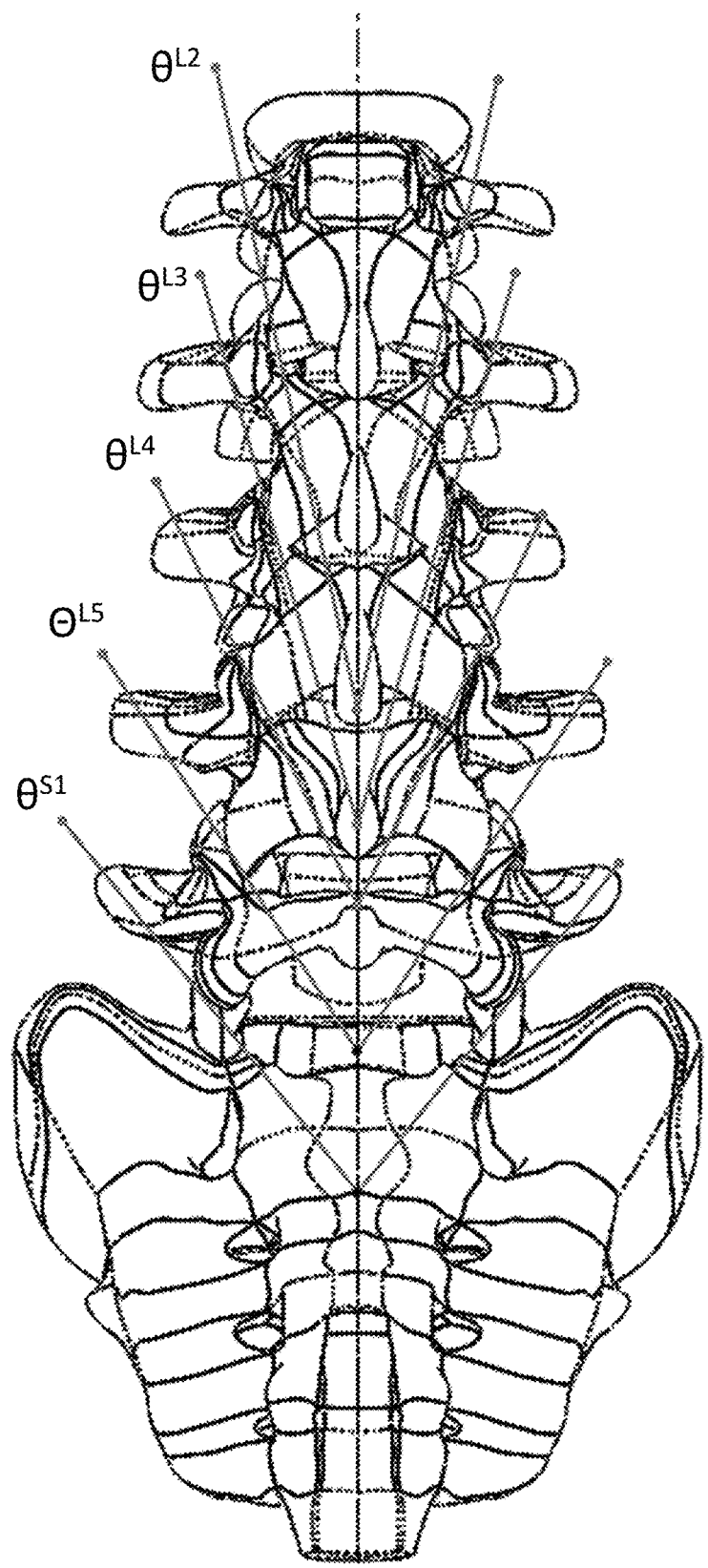
FIG. 6A depicts an anterior-posterior (A/P) view of the lower spinal segment of FIG. 5, showing typical facet joint angles for each lower spinal level.
Figure 6B:
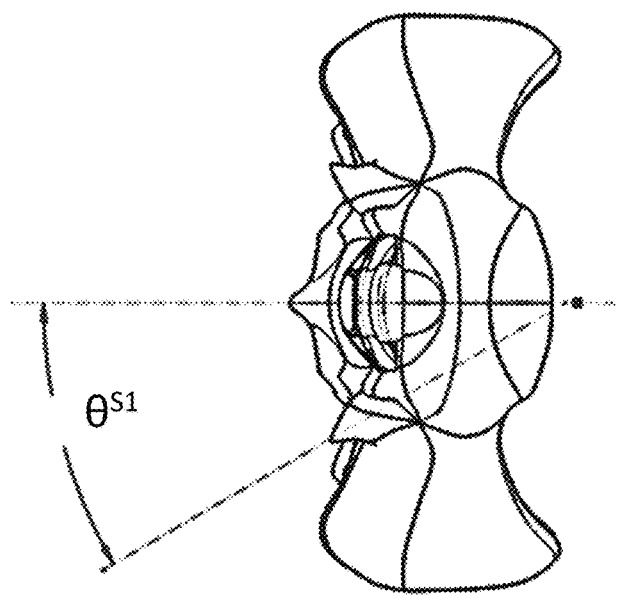
FIGS. 6B through 6G depict typical facet joint angles for lower vertebrae S1, L5, L4, L3, L2, and L1.
Figure 6C:
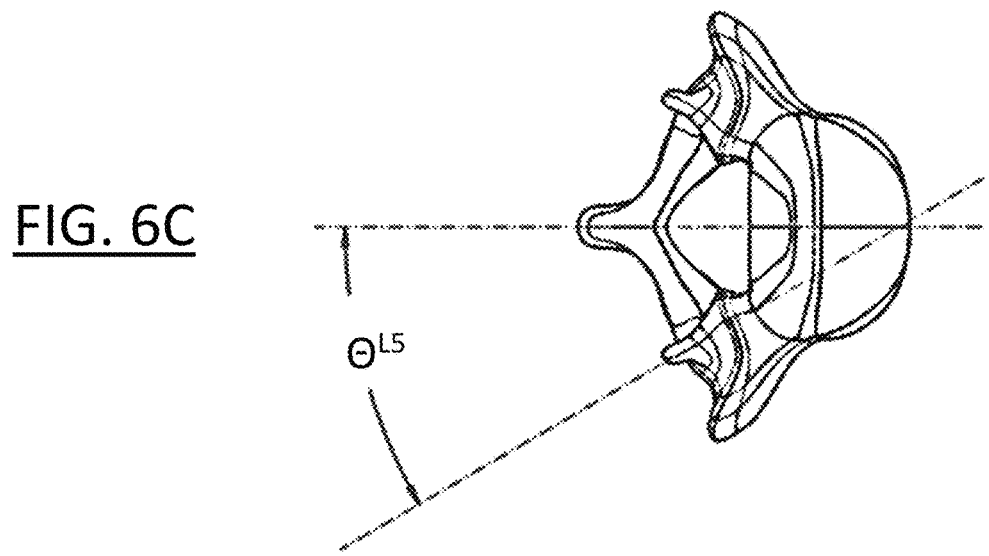
Figure 6D:
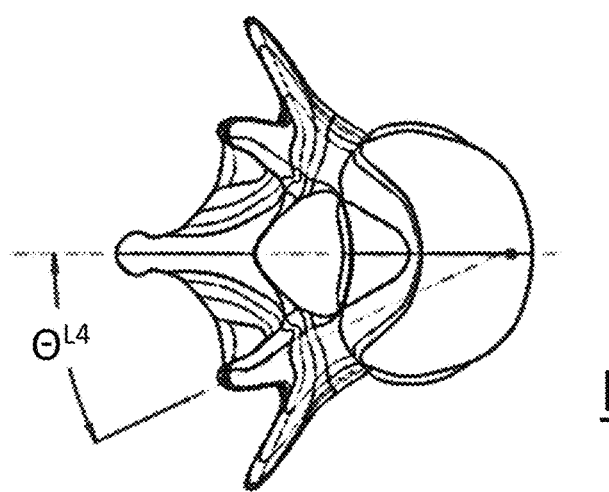
Figure 6E:
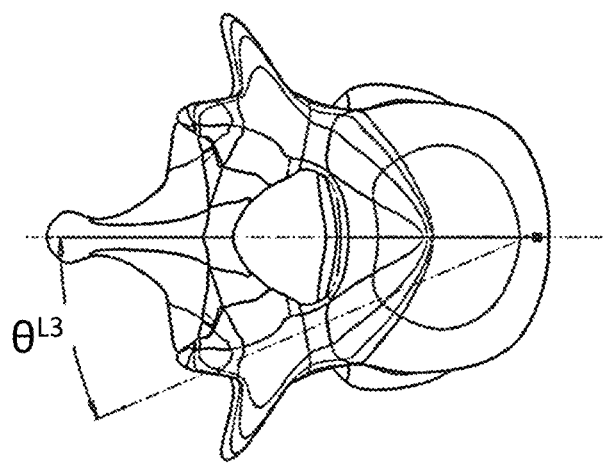
Figure 6F:
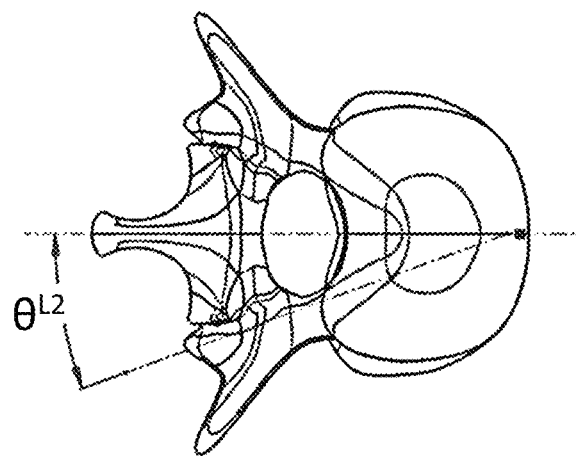
Figure 6G:
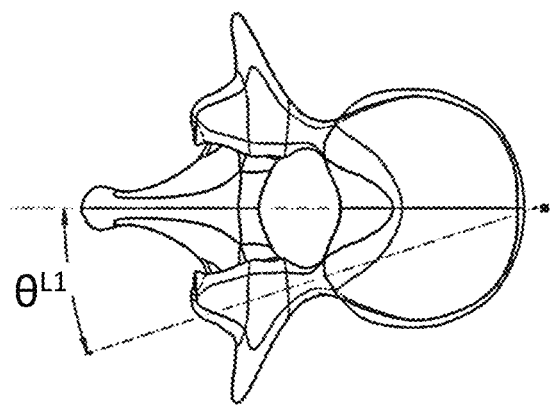

FIG. 6A depicts an anterior-posterior (A/P) view of the spinal segment of FIG. 5, showing typical facet joint angles for each lower spinal level. Because the facets and related spinal structures of each vertebral level are typically angled somewhat differently, and the implants of the current invention desirably utilize some portion of the pedicular support structures of a given level to improve implant stability and durability, the implant components will desirably accommodate these angular differentials, which in the disclosed figures are. As best seen in FIGS. 6A and 6B, one exemplary angle $\theta^{S1}$ (referred to as the transverse pedicle angle) for the S1 pedicles (relevant to an implant in the L5-S1 level) is approximate degrees from midline, or a "toe-in" angle (between the two pedicles of the vertebral body) of approximately 60° therebetween. FIGS. 6A and 6C depict an exemplary pedicle angle $\theta^{L5}$ for L5 (relevant to an implant in the L4-L5 level) of approximately 30 degrees from midline, or a "toe-in" angle of approximately 60° therebetween. FIGS. 6A and 6D depict an exemplary pedicle angle $\theta^{L4}$ for L4 (relevant to an implant in the L3-L4 level) of approximately 23 degrees from midline, or a "toe-in" angle of approximately 50° therebetween. FIGS. 6A and 6E depict an exemplary pedicle angle $\theta^{L3}$ for L3 (relevant to an implant in the L2-L3 level) of approximately 23 degrees from midline, or a "toe-in" angle of approximately 46° therebetween. FIGS. 6A and 6F depict an exemplary pedicle angle $\theta^{L2}$ for L2 (relevant to an implant in the L1-L2 level) of approximately 20 degrees from midline, or a "toe-in" angle of approximately 40° therebetween. FIG. 6G depicts an exemplary pedicle angle $\theta^{L1}$ for L1 (relevant to an implant in the T12-L1 level) of approximately 18 degrees from midline, or a "toe-in" angle of approximately 36° therebetween. Of course, it should be understood that the vertebral bodies herein are depicted in an "idealized" fashion, as natural anatomical variations within the patient population and injury and/or degradation of an individual patient's vertebral bodies will result in vertebral bodies that are generally non-symmetrical—that is, the left and right pedicles of an actual vertebral body are unlikely to be perfectly symmetrical and/or uniform as measured from the vertebral midline.

In various embodiments, the devices disclosed herein can be utilized in a variety of positions and/or placements, including those previously discussed. In various additional exemplary embodiments, implant component pairs such as those described herein can be utilized at multiple vertebral levels of the spine, including placement at a transverse pedicle angle $\theta^{S1}$ of from 20 degrees to 40 degrees, e L5 of from 10 degrees to 35 degrees, $\theta^{L4}$ of 10 degrees to 25 degrees, $\theta^{L3}$ of 5 degrees to degrees, $\theta^{L2}$ 5 degrees to 20 degrees and/or $\theta^{L1}$ of zero degrees to 15 degrees.

Figure 7A:
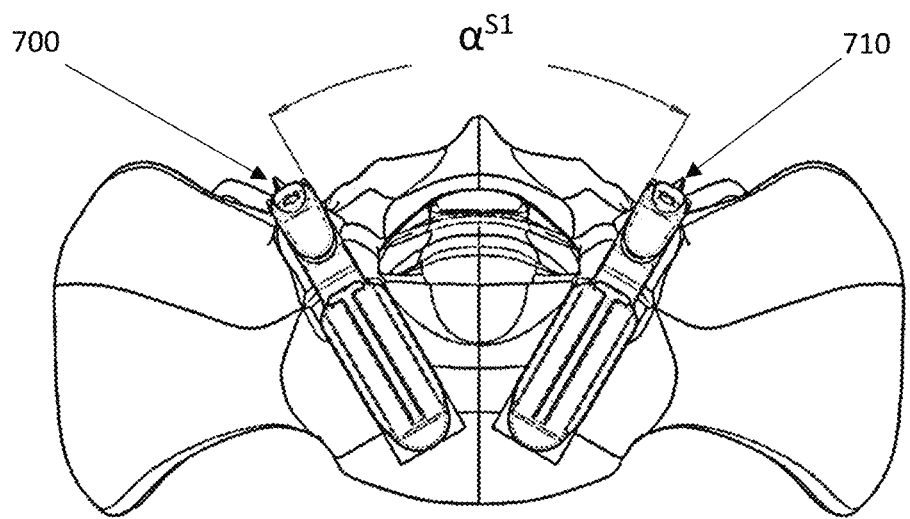
FIG. 7A depicts a cephalad-caudad view of an exemplary S1 vertebral body.
Figure 7B:
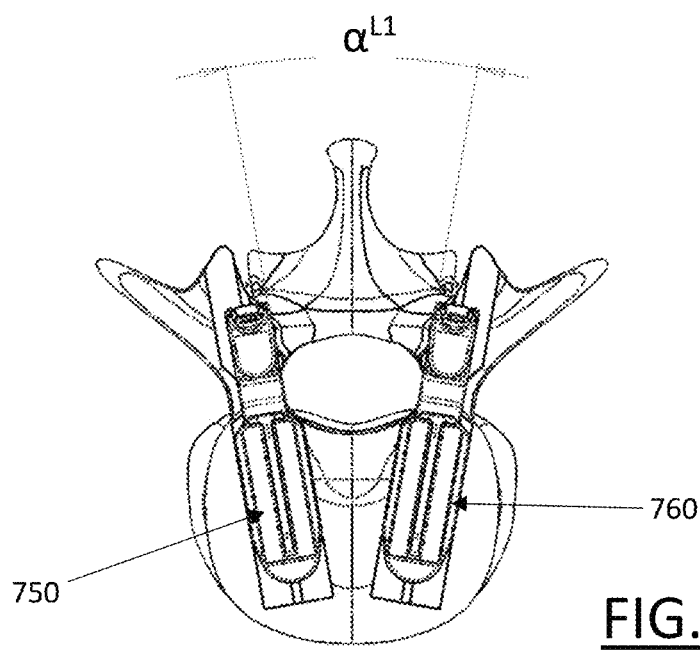
FIG. 7B depicts a cephalad-caudad view of an exemplary L1 vertebral body.

FIG. 7A depicts a cephalad-caudad view of an S1 vertebral body, with a pair of intervertebral implants 700 and 710 implanted therein. In this embodiment, each of the intervertebral implants 700 and 710 are desirably aligned along a respective right and left pedicle of the vertebral body, which results in an intervertebral construct having a toe-in angle $\alpha^{S1}$ of approximately 60 degrees. This first component arrangement will desirably provide a significant resistance to shear loading of the implants and the spinal level, as such high shear loading is common in this spinal level. In contrast, FIG. 7B depicts a cephalad-caudad view of a L1 vertebral body, with a pair of intervertebral implants 750 and 760 implanted therein. In this embodiment, each of the intervertebral implants 750 and 760 are desirably aligned along a respective right and left pedicle of the vertebral body, which results in an intervertebral construct having a toe-in angle $\alpha^{L1}$ of approximately 36 degrees. This second component arrangement allows for less resistance to shear loading of the implants at this level, as high shear loading is much less likely to occur at this spinal level. However, the unique design of the implant components described herein allow for implantation at multiple levels of the spine, as it is highly desirable to have a single intervertebral implant design that can accommodate a wide range of variations in pedicle angles and/or lordotic angles of the vertebral bodies in which they are implanted.

Figure 7C:
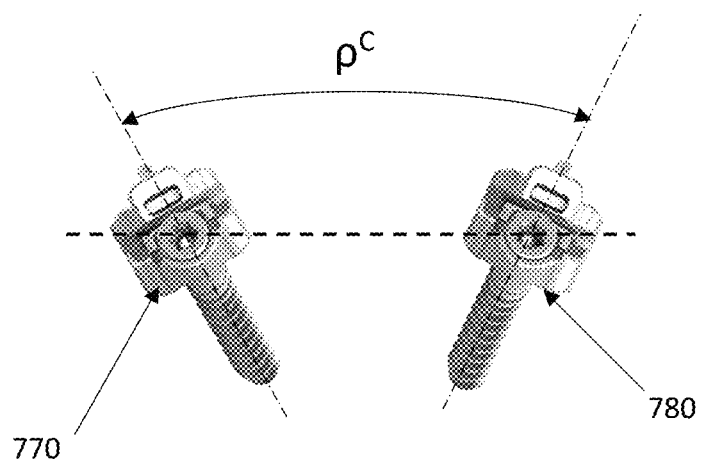
FIG. 7C depicts exemplary component pairs implanted in a vertebral level with a significant variation in coronal plane component pair alignment.
Figure 7D:
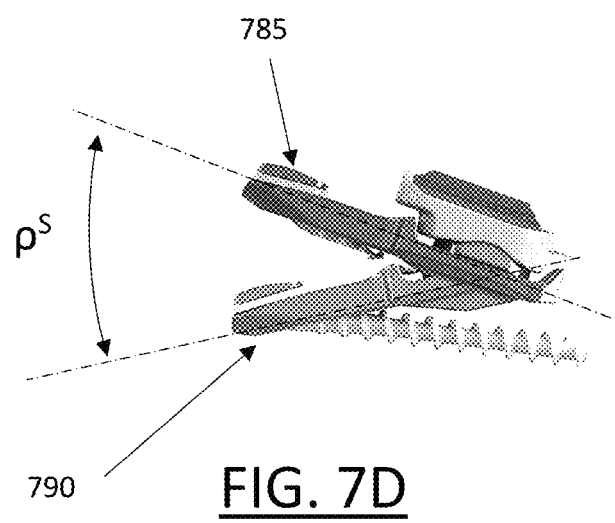
FIG. 7D depicts exemplary component pairs implanted in a vertebral level with a significant variation in sagittal plane component pair alignment.

In addition to being capable of use at multiple levels of the spine, the disclosed implants further allow significant alignment variations with little no effect on the functionality of the construct. For example, as depicted in FIG. 7C, the component pairs 770 and 780 can be implanted in a vertebral levels with a significant variation $\rho^c$ in coronal plane alignment (in some embodiments up to 20 degrees out of alignment in the coronal plane) and still function to allow a desired amount of flexion and/or extension for the treated vertebral level. FIG. 7D depicts the component pairs 786 and 790 implanted in a vertebral levels with a significant variation $\rho^s$ in sagittal plane alignment (in some embodiments up to 20 degrees out of alignment in the coronal plane) and still function to allow some amount of flexion and/or extension for the treated vertebral level.

Figure 8A:
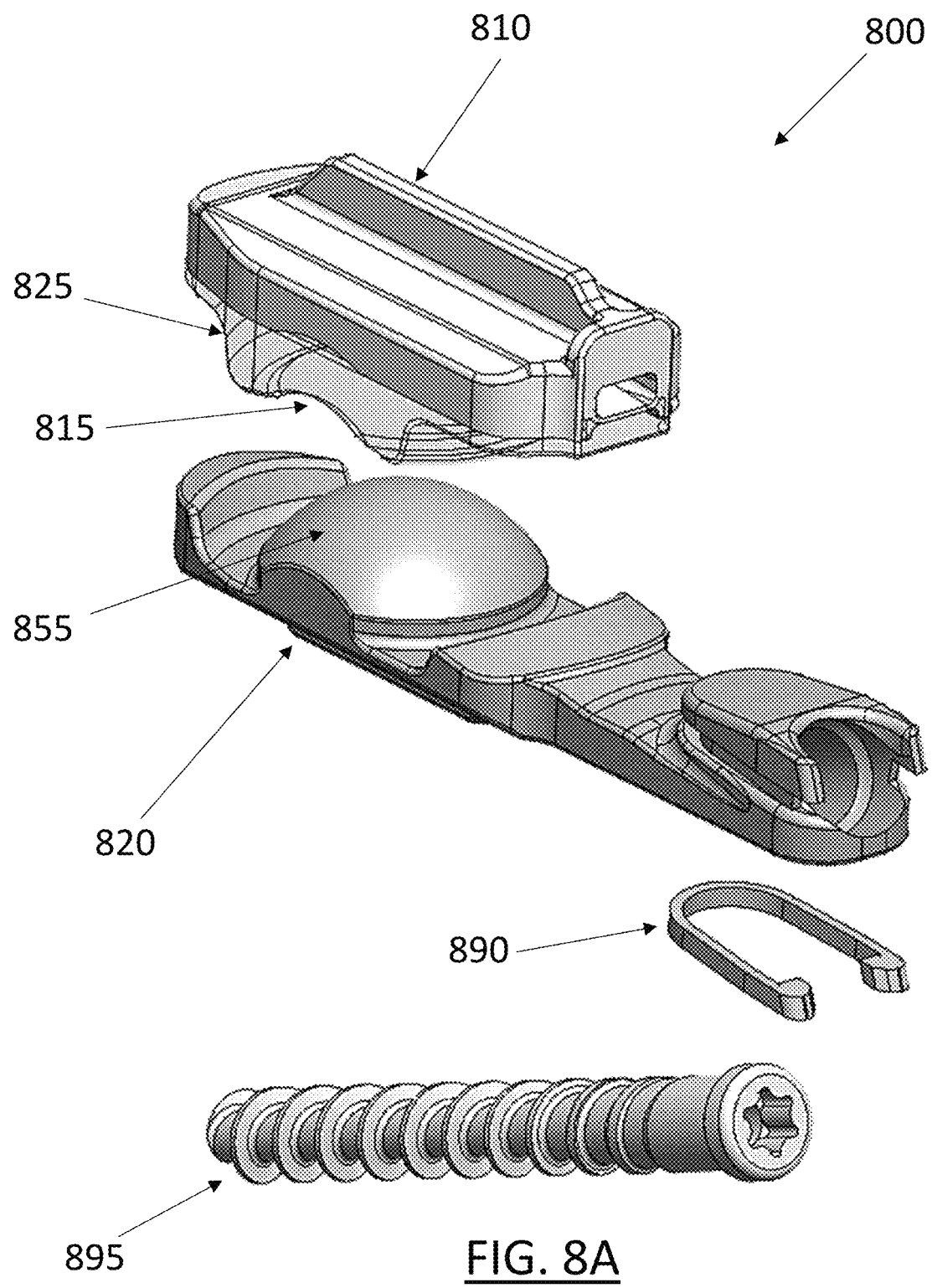
FIG. 8A depicts an exploded view of one exemplary embodiment of an intervertebral implant.
Figure 8B:
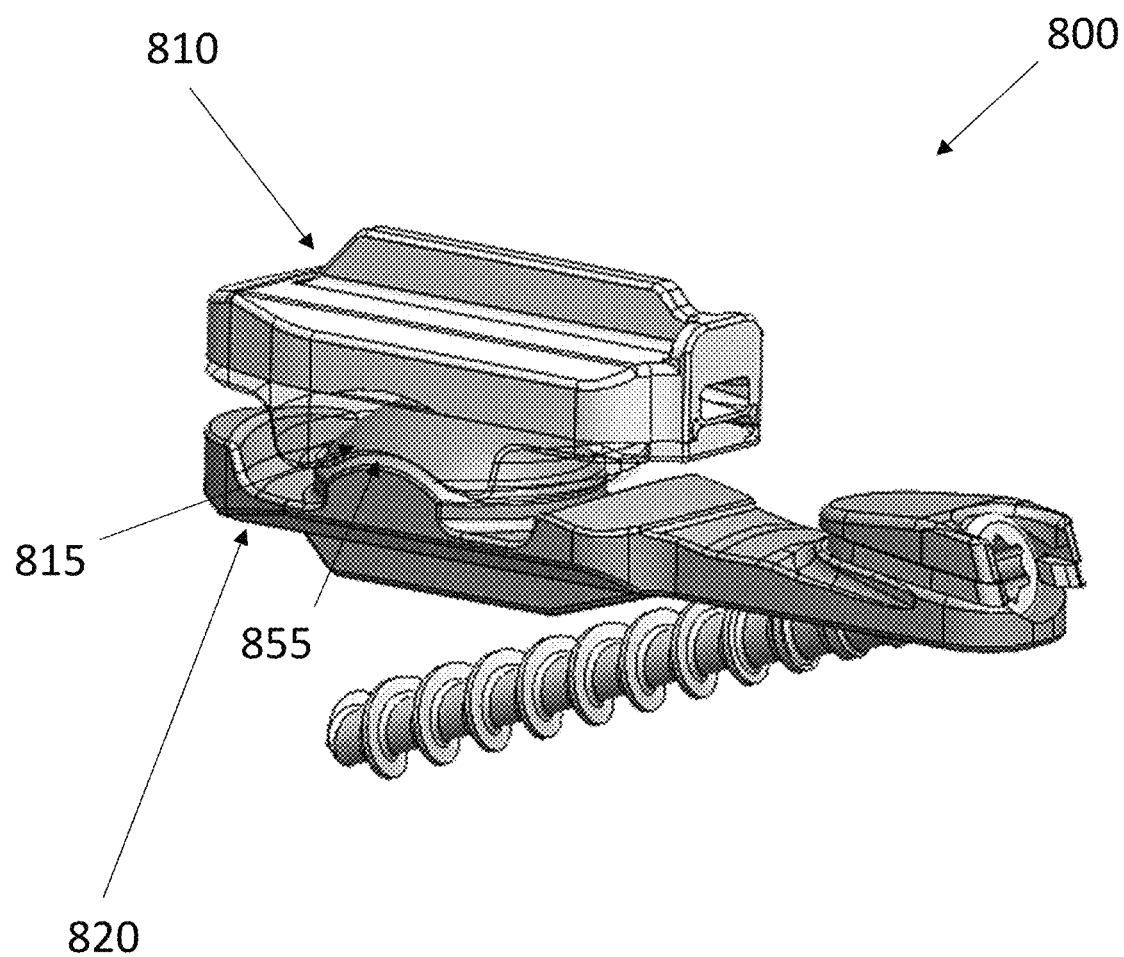
FIG. 8B depicts a fully assembly view of the intervertebral implant of FIG. 8A.

FIGS. 8A and 8B depict exploded and fully assembled perspective view of an intervertebral implant 800 which provides for significant resection of a vertebral body and/or pedicle (including resection of a superior endplate and/or cortical rim portion of an inferior vertebral body, as well as optionally preparation of only part of a pedicle) and associated spinal structures, while still preserving stability and/or motion in the spinal joint. The intervertebral implant 800 can include an upper joint component 810 and a lower joint component 850. The upper joint component 810 desirably includes an articulation surface 815, which may be smooth, concave, and/or generally spherical in shape. The lower joint component 850 can similarly include an articulation surface 855, which may be smooth, convex, and/or generally spherical in shape. As assembled, the articulation surface 815 may engage the articulation surface 855 to produce a ball-and-socket style anterior joint.

As defined herein, a "spherical" shaped surface could include any curved surface having a uniform radius of curvature and may refer to a spherical cap or a segment of a sphere. In various alternative embodiments, non-spherical curved surfaces may function as articulation surfaces to impart specific limits to the range of motion of the prosthetic device. In still another alternative embodiment, the joint may be inverted with the upper articulation surface having a convex shape and the lower articulation surface having a concave articulation surface.

Figure 9:
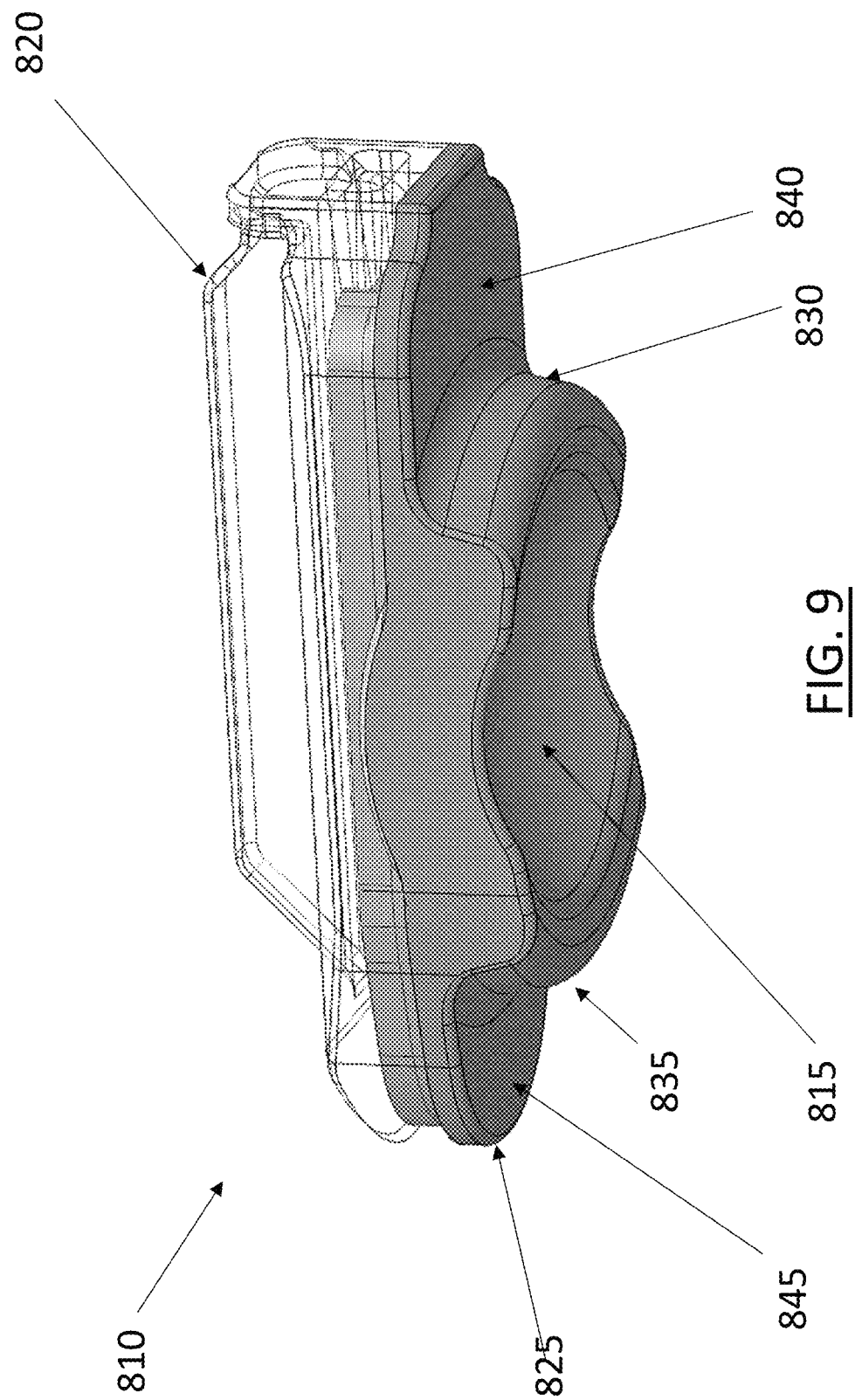
FIG. 9 depicts a perspective view of an exemplary embodiment of an upper component assembly.

As best seen in FIGS. 8A and 9, the upper joint component 810 can include an upper joint body 820 and an articulating insert 825 (depict as transparent in FIG. 8A and solid in FIG. 9). In this embodiment, the articulating insert 825 can be formed from a durable, flexible material such as ultra-high-molecular-weight polyethylene (UHMWPE) or similar material, while the upper joint body 820 can comprise a metallic component to which the insert 825 is attached. A corresponding articulating surface 855 of the lower joint component 850 can desirably be formed from metal (i.e., chrome cobalt) or a ceramic material, such that one bearing component (i.e., the upper bearing component) is significantly more compliant than the other bearing component (i.e., the lower bearing component). This arrangement can provide a better performing joint which experiences less wear and/or generates less wear debris than many other implant designs, as the concave UHMWPE "cup" can easily conform to or otherwise accommodate the harder ball or other convex surface, providing better wear performance and reducing the potential for stress concentrations and/or point loading of the joint.

In the present invention, various embodiments of these disclosed spinal implants may perform better, experience less wear and/or generate less wear debris if the "softer" component is on the concave side of the bearing couple (including spherical ball-in-cup type bearing couples as well as non-spherical and/or curved bearing couples) and the "harder" component is on the convex side. Such an arrangement can allow the cup or other concave receiving surface to "conform to" or otherwise accommodate the harder ball or other convex surface, providing better wear performance and reducing the potential for stress concentrations and/or point loading. In contrast, the existing configurations of many implants in the prior art allow for a variety of suboptimal effects, including the potential for rim loading of surfaces within the bearing, which can greatly accelerate wear and/or failure of the bearing couple.

While various embodiments disclosed herein can include bearing couples of identical and/or similar materials, In other embodiments a spinal joint replacement can incorporate one or more bearing couples having dissimilar bearing surface materials (i.e., the dissimilar materials having dissimilar hardness or durometer measures in various embodiments), which in at least one embodiment includes a metal component that engages with a non-metallic component such as an ultra-high-molecular-weight polyethylene (UHMWPE) component or similar material, where one bearing component is significantly more compliant than the other. In various embodiments, the present invention can be utilized with a lumbar or cervical disc replacement implant, where the bearing surfaces can be arranged and configured in the disclosed manner. If desired, a posterior lumbar joint replacement can be provided, wherein the upper concave UHMWPE structure and/or surface may be fixed within a bone ingrowth shell of 3D printed or similar porous titanium to transmit stress and desirably in-grow biologically to the upper end plate of the upper vertebrae, and a 3D printed or similar titanium inferior component can be provided with a tail that travels down the axis of the pedicle, to transmit loads and biologically fix to the lower end plate and/or cortical/cancellous bone of the lower vertebrae. If desired, the lower component could optionally have a Cobalt Chrome (CoCr) or similar bearing cap to wear against and/or articulate with the upper UHMWPE component.

In addition to the polyethylene articulation surface 815, the insert can also incorporate various peripheral structures such as retention surfaces 830, 835 and motion limiters or bumpers 840 and 845, which in this embodiment are depicted as recessed surfaces and shoulders. As best seen in FIGS. 10A and 10B, the lower joint component 850 can also include retention surfaces 860, 865 and bumpers or motion limiters 870, 875 which in this embodiment are corresponding recessed surfaces and upwardly protruding extensions, which are spaced apart from the articulation surface 855. As will be described in greater detail below, the pairs of motion limiters 840, 845 and 870, 875 and the retention surfaces 830, 835, 860 and 865 desirably allow significant range of motion between the upper and lower joint components 810 and 850 in a variety of orientations, while constraining and/or limiting movement to a desirable range, thereby preventing or limiting the dislocation of the joint formed by the implant components. Because these structures are formed from polyethylene on the insert, however, the polymeric material helps to absorb and/or dissipate the impact on the metallic surfaces to some degree, thereby reducing peak loading of the implant and/or the various bone anchors securing the implant to the patient's anatomy.

In various exemplary embodiments, the lower joint component 850 can include a bridge component 875 (see FIG. 10B), which desirably extends posteriorly from the intervertebral disc space between the vertebral bodies, with a lower surface that abuts and/or engages with at least a portion of a pedicle of the vertebral body to a distal end 880 of the lower joint component 850.

The distal end 880 of the bridge 875 may include a connection component 885, which in this embodiment is a passage for accepting a pedicle screw-type fastener. In this embodiment, the fastener can be a bone screw, however in alternative embodiments, fasteners such as nails, staples, or other mechanical or chemical fasteners may be suitable. The orientation of the connection component 885 desirably permits the fastener to become inserted along and/or parallel to a pedicle (i.e., extrapedicularly), such that the screw may travel a path obliquely angled or skewed away from a central axis defined through a pedicle. The fastener may be threaded across a portion of the pedicle and into the vertebral body. Extrapedicular fixation may be any fixation into the pedicle that does not follow a path down a central axis defined generally posterior-anterior through the pedicle. In this embodiment, the screw passes through a wall portion of the pedicle, whereby it may achieve strong cortical fixation. In all embodiments, the fasteners may be at least partially recessed so as not to interfere with articulations, soft tissues, and neural structures.

As installed, the bridge 875 and the fastener may limit excessive movement of the device, particularly during flexion/extension motions. Additionally, the bridge may distribute the loads on the lower vertebra and/or cortical bone of the pedicle, thereby reducing any opportunity for subsidence of the lower joint component into the vertebral body, even where the anterior portions of the implant may be primarily supported by cancellous bone exposed by removal of the endplate material.

If desired, the connection component 885 may further include an optional locking clip 890 (see FIG. 8A), which in this embodiment is an elastically deformable C-shaped structure which holds a fastener 895 in place, resisting any backward disengagement of the fastener 895, particularly when the joint is in motion. It is understood that in alternative embodiments, the locking clip may be a cap, a clamp, an adhesive, or other suitable mechanical or chemical systems for limiting movement of the fastener.

Figure 11A:
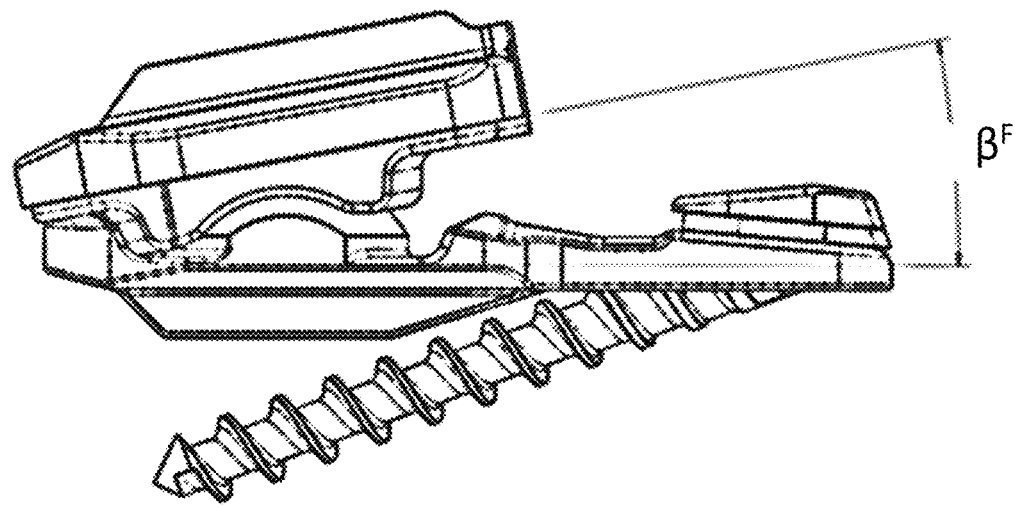
FIGS. 11A and 11B depict sides of exemplary component pairs in full flexion and full extension.
Figure 11B:
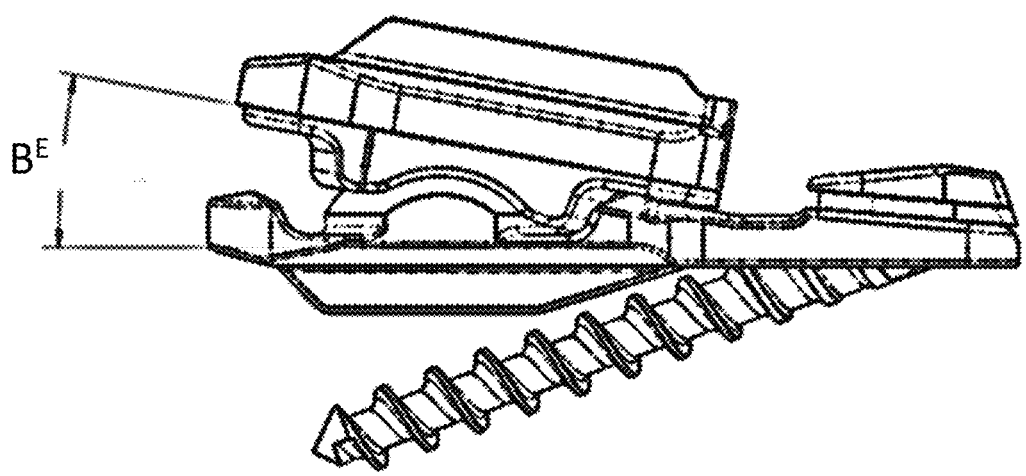
Figure 12A:
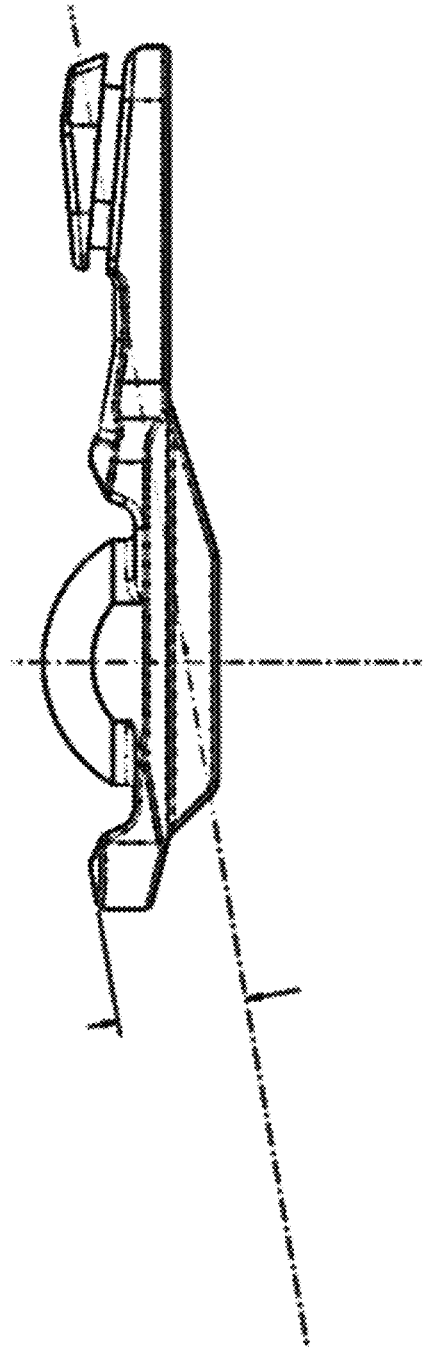
FIGS. 12A and 12B depict side views of the bumper alignment of a lower component assembly for flexion and extension.
Figure 12B:
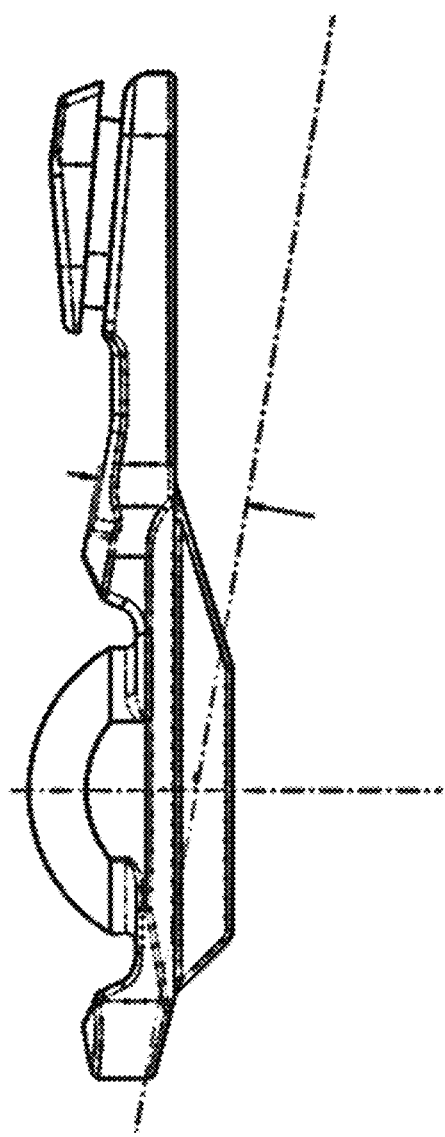

As best seen in FIGS. 11A and 11B, in various embodiments the upper and lower joint components will desirably provide at least 10 degrees of flexion $\beta^F$, and at least 10 degrees of extension $\beta^E$ along the articulating surfaces before the motion limiters or bumpers on the upper and lower joint components come into respective contact. In at least one exemplary embodiment, these bumper surfaces can desirably be gently curved surfaces which are angled and/or tilted relative to a neutral axis of the upper and lower joint components, such that the plane of the bumper surface is offset and parallel to a plane passing through the axes of revolution between the upper and lower joint components, which is best depicted in FIG. 12A for flexion and FIG. 12B for extension.

Figure 13A:
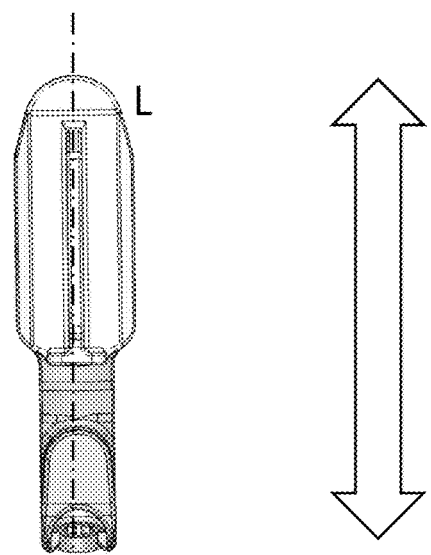
FIGS. 13A through 13C depict an allowable range of motion for the upper and lower joint component assembly for various pedicle angles.
Figure 13B:
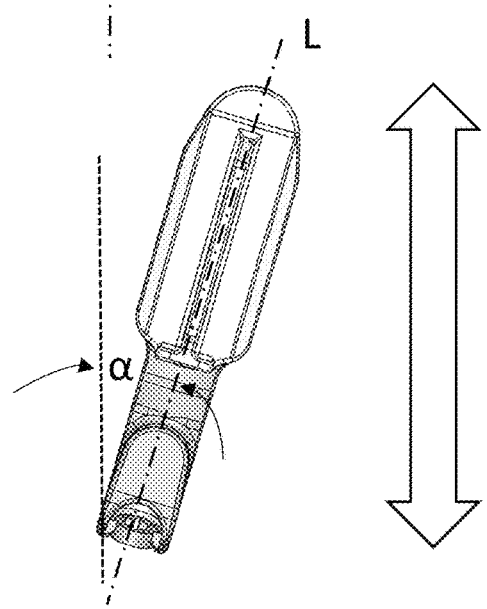
Figure 13C:
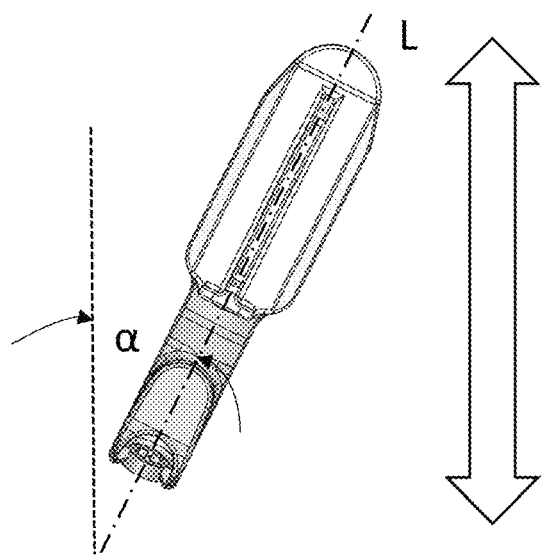

FIGS. 13A through 13C depict examples of how the upper and lower joint components of the present invention are designed to allow for a desired range of flexion and extension, regardless of the pedicle angle in which they are implanted. In the embodiment of FIG. 13A, flexion (i.e., forward) movement and extension (i.e. backward) movement of the implant occurs along the longitudinal axis L of the implant (in the directions of the movement axis indicated by the arrow). In this embodiment, this movement causes the center of the bumpers of the upper and lower joint components (i.e., front bumpers for flexion and rearward bumpers for extension) to eventually come into contact and generally constrain further movement of the implant at its rotation limits (which may include contact between the entirety of the upper and lower bumpers in some embodiments). In FIG. 13B, flexion and extension occur at a more narrow angle α to the longitudinal axis L of the implant, which generally induces the more leftward sides of the front bumpers to contact in flexion, and the more rightward sides of the rear bumpers to contact and generally constrain movement of the implant at its rotation limits. In FIG. 13C, flexion and extension occur at a greater angle α to the longitudinal axis L of the implant, which generally causes the most extreme leftward sides of the front bumpers to contact in flexion, and the most extreme rightward sides of the rear bumpers to contact and generally constrain movement of the implant at its rotation limits.

Figure 14A:
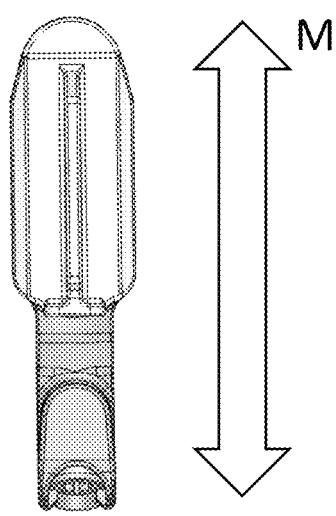
FIGS. 14A and 14B depict functional aspects of mis-aligned component assemblies.
Figure 14B:
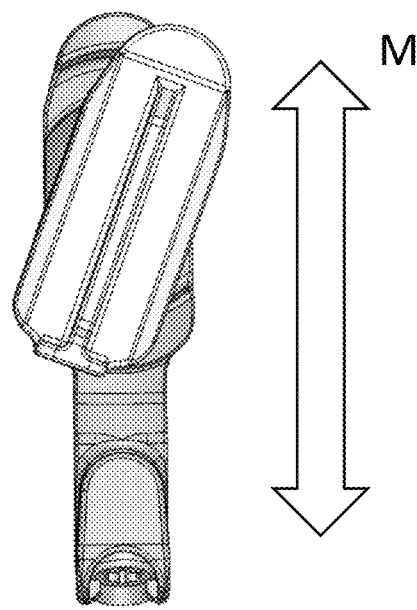

FIGS. 14A and 14B depict how the disclosed implant components can accommodate component misalignment and/or movement, yet still function in a normal manner. As best seen in FIG. 14A, the upper and lower components can move along axis M in a desired manner, where the implant components are aligned. However, FIG. 14B shows that a similar range of motion of the upper and lower components can still be achieved where the upper and lower components are not fully aligned, such as where the upper component may be rotated clockwise relative to the lower components. While one objective of the disclosed surgical procedure is to desirably align the upper and lower components during device implantation, it is possible that anatomical constraints will obviate the surgeon's ability to make such parallel alignment during implantation, or post-surgical migration, rotation and/or subsidence of an individual implant component and/or component pair will alter such alignment over time. In such a case, the implant will desirably accommodate such changes and will continue to provide a desired degree of motion to the treated spinal level.

Figure 14C:
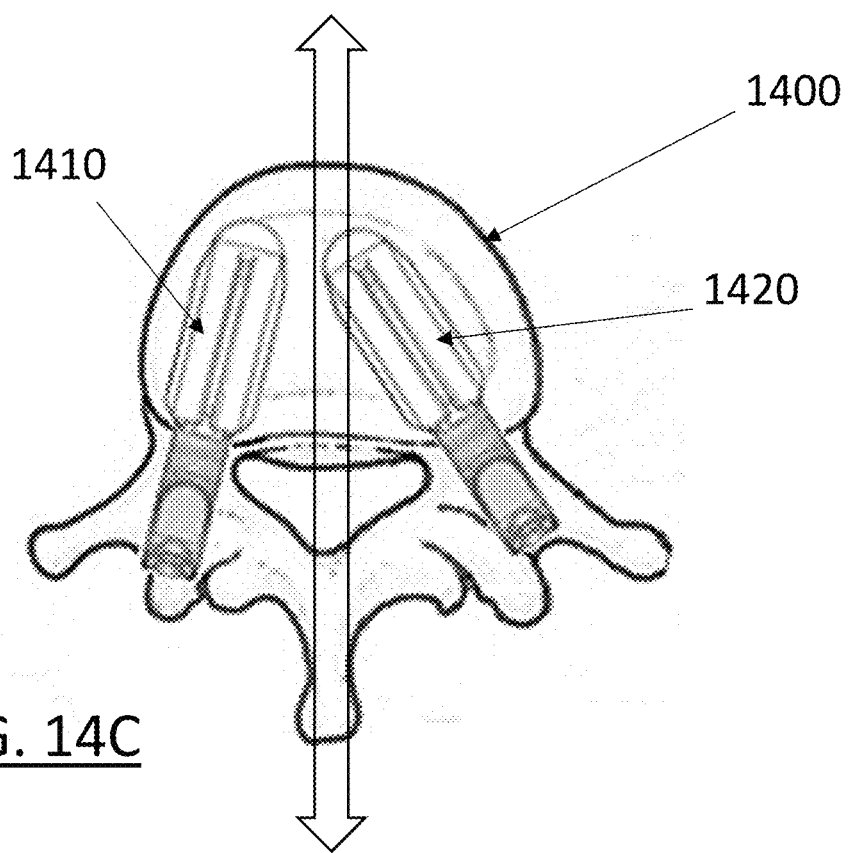
FIG. 14C depicts a cephalad view of a pair of upper and lower joint component assemblies implanted at differing toe-in angles.
Figure 14D:
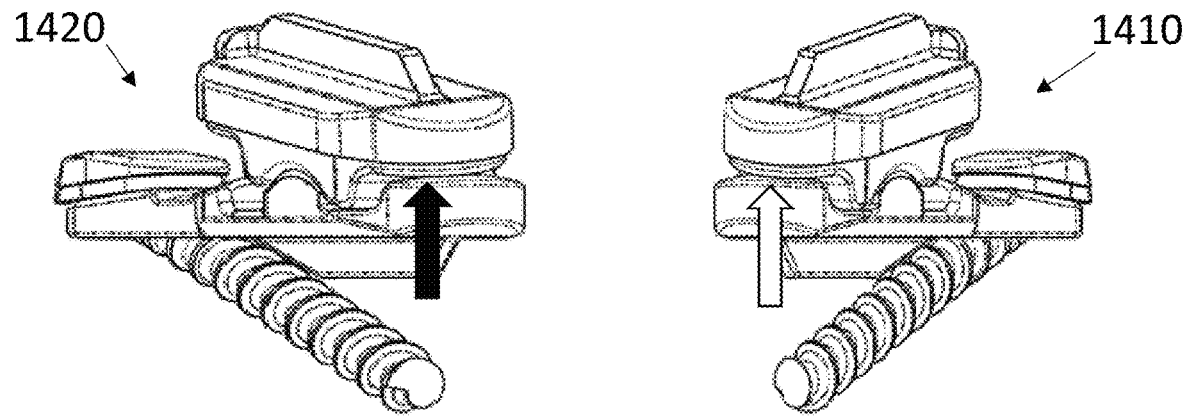
FIG. 14D depicts the upper and lower joint component assemblies of FIG. 14C from an anterior-posterior (A/P) viewpoint during a flexion motion.

FIG. 14C depicts a cephalad view of pair of implant component pairs 1410 and 1420 in a vertebral body 1400, where a toe-in angle of the implant component pair 1420 at the right side of the vertebral body is significantly greater than a toe-in angle of the implant component pair 1410 at the left side of the vertebral body, with FIG. 14D depicting the implant component pairs 1410 and 1420 of FIG. 14C from an anterior-posterior (A/P) viewpoint during a flexion motion. It should be understood that such differences in toe-in angles in a given vertebral body can be quite common, due to a variety of factors (including those already discussed). However, regardless of implant positioning and/or alignment, the present inventions will desirably provide an adequate range of motion to the treated spinal level. As best seen in FIG. 14D, the cooperation between the component pairs allows for flexion and/or extension of the treated vertebral level in a desired anterior-posterior direction, with the implant component pair 1420 having the greater toe-in angle providing for bumper impingement towards a side of implant (in a region indicated by the black arrow), while the implant component pair 1410 having the lesser toe-in angle provides for bumper impingement closer towards a central region of the implant (in a region indicated by the white arrow). In this manner, therefore, the various implant components described herein can provide a desired range of motion for a treated spinal level, regardless of implant alignment and/or natural anatomical variation. In one exemplary embodiment, shown in Table 1 below, the implant can allow significant flexion and/or extension to an individual construct pair for a variety of toe-in angulations.

| FIG. 1: Degrees of Flexion/Extension | | |
|---|---|---|
| Toe In Angle | Flexion angle | Extension Angle |
| 0° | 10° | 10° |
| 15° | 10.5° | 10.5° |

-continued

FIG. 1: Degrees of Flexion/Extension

| Toe In Angle | Flexion angle | Extension Angle |
|---|---|---|
| 30° | 11.5° | 11.5° |
| 45° | 14° | 14° |

If desired, the motion allowed by one or more motion limiters and/or bumpers of one of more of the implant components may be shaped to provide a greater or lesser range of flexion/extension motion. For example, a surface on the motion limiter angled away from the articulation surface may permit greater flexion motion than would a motion limiter surface parallel to an axis of the spine.

Figure 15A:
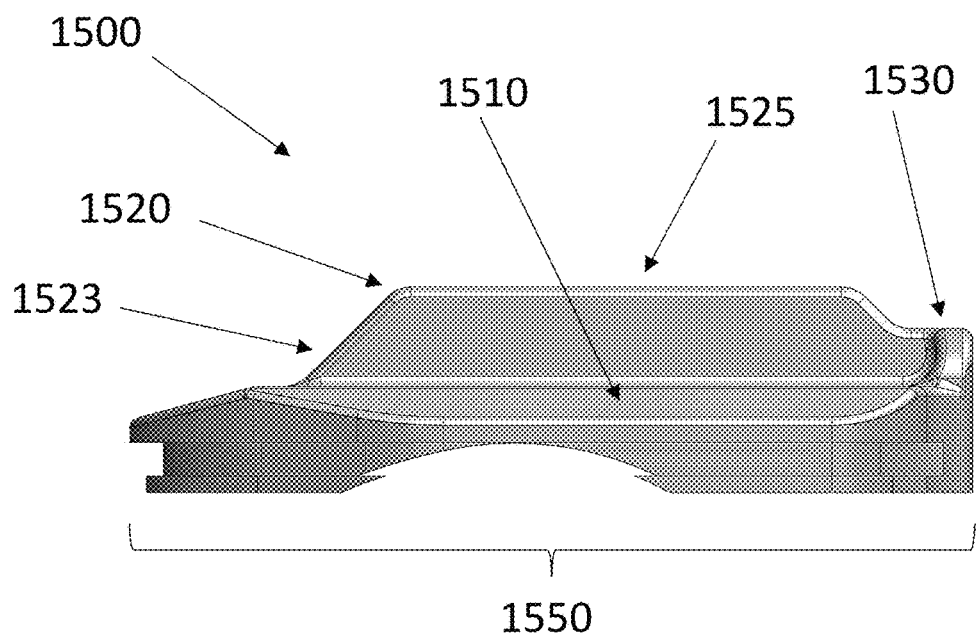
FIGS. 15A through 15C depict various views of an upper joint component without an articulating insert.

FIG. 15A depicts a side view of an upper joint component 1500 having an outer contact surface 1510 for interfacing with a vertebral endplate (not shown). The upper joint component 1500 may further include an upper keel 1520 extending from the outer contact surface 1510 and comprising a tapered leading edge 1523, an elongated portion 1525 and a posterior tab 1530. The elongated portion 1525 can provide the prosthetic device with greater stability in a portion of the hard cortical bone of the outer wall of a vertebral body, and can extends to the posterior edge of the upper joint component to provide additional stability where it meets with the posterior tab 1530. The posterior tab 1530 can desirably extending upward from a posterior edge of the outer contact surface 1510. In this embodiment, the tab 1530 may be generally perpendicular or slightly acutely angled relative to the contact surface. The tab 1530 may be integrally formed with or otherwise abut the posterior end of the upper keel 1520. If desired, the posterior tab may serve as a stop to prevent the device from being inserted too far anteriorly into the intervertebral disc space. The position of the tab may be monitored with fluoroscopy or other visualization methods during surgery to determine the progress of the implantation and to confirm when the device has been completely implanted with the posterior tab in contact with a posterior wall of the vertebral body. Because the position of the posterior tab may be fixed relative to a center of rotation of the joint formed by the various articulation surfaces, the location of the posterior tab may serve as an indicator of the location of the center of rotation. After the surgeon has determined the desired location for the center of rotation, the upper joint component may be selected so that as the posterior tab is positioned against the posterior wall of the vertebral body, the center of rotation is moved into the desired predetermined location. In various alternative embodiments, the upper keel may be longer or shorter to achieve desired stability. If desired, the lower joint component may similarly include a lower keel extending from an outer contact surface, if desired. In various alternative embodiments, the width of the keel may vary. For example, the keel may taper or have an undulating wave form. In still another alternative, the keel may be perforated or porous to promote bone ingrowth.

Figure 15B:
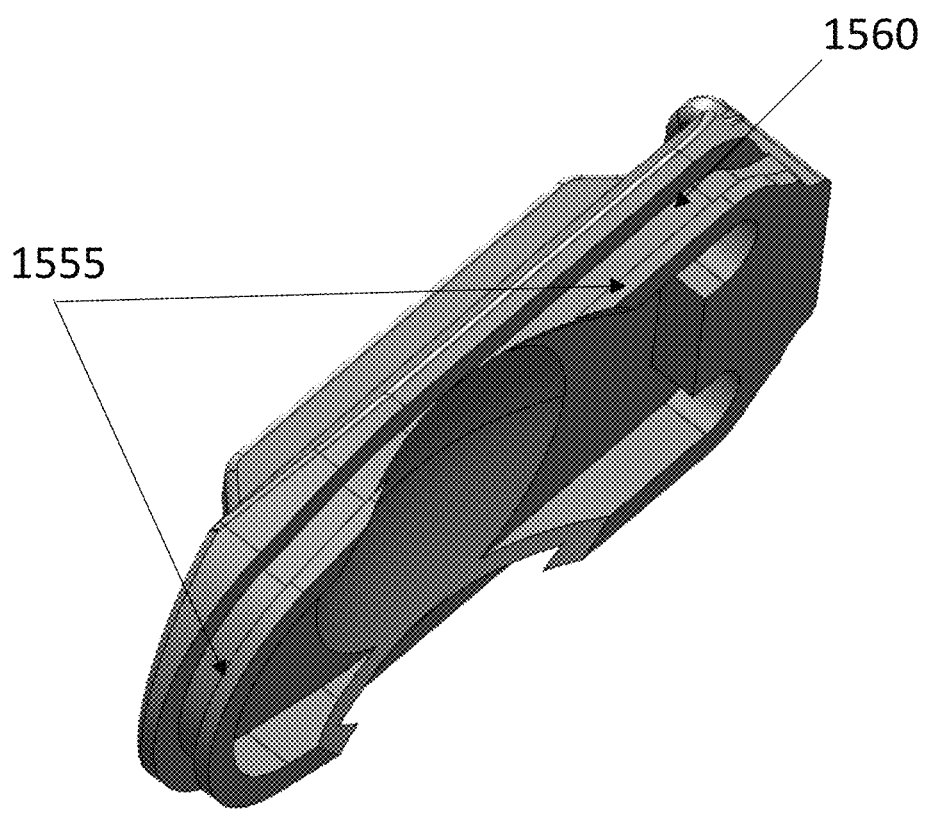
Figure 15C:
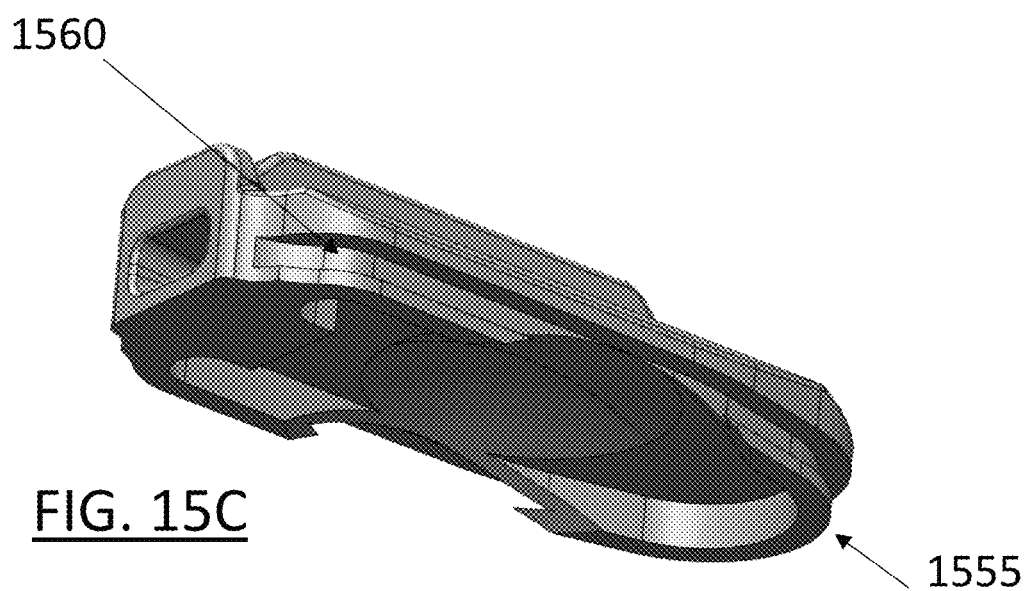

FIGS. 15A through 15C depict an upper joint component 1500 with a lower engagement surface 1550, which in these figures desirably engages with an articulating insert (which is not installed in these figures). The lower engagement surface 1550 desirably includes a peripheral ridge 1555 and ridge groove 1560. In this embodiment, the articulating surface can comprise an ultra-high-molecular-weight polyethylene (UHMWPE) or similar material, which is desirably over-molded onto the lower engagement surface 1550 of the upper joint component 1500 (to desirably create the implant of FIG. 9). In various embodiments, the polyethylene material will desirably over mold and be engaged with the peripheral ridge 1555 and ridge groove 1560, such that when the polyethylene cools and shrinks slightly during the molding and/or cross-linking processes, the polyethylene will become more tightly engaged with and secured onto the peripheral ridge 1555 and ridge groove 1560.

The size and shape of the various joint components described herein may be limited by the constraints of a posterior surgical approach. For example, the upper and lower joint components may be configured to cover a maximum vertebral endplate area to dissipate loads and reduce subsidence while still fitting through the posterior surgical exposure, Kambin's triangle, and other neural elements. To achieve maximum surface coverage, the material of the anterior joint components may extend anteriorly from the articulation surfaces, respectively. The width of the upper and lower joint components may also be selected to desirably pass through Kambin's triangle and to co-exist with the neural elements, yet provide sufficient cross-sectional area to the pedicle structures for additional support.

In alternative embodiments, the upper and lower joint components may be provided in various heights. For example, the height of the upper component may be increased by manufacturing the component with a thickened contact surface. Likewise, material may be added to increase the overall height of the lower component. Providing the components in a variety of selectable heights may allow the surgeon to create the appropriate tension within the joint to both promote bone growth into the upper and lower components and to achieve a desired range of motion. In still other alternative embodiments, the heights of the upper and lower joint components may increase or decrease along the length of the component to create a desired lordosis or kyphosis. The ability to modify the resulting angle between the upper and lower vertebral contact surfaces may allow the surgeon to address variations among patient anatomies or between levels of the vertebral column, such as at the lumbosacral joint (L5-S1). Allowing the surgeon to vary the height, angulation, and performance of the prosthetic device based on the vertebral level or the patient's anatomy may ensure a better fit and a better prognosis for the patient.

For all of the embodiments described herein, the prosthetic device may be formed of any suitable biocompatible material including metals such as cobalt-chromium alloys, titanium alloys, nickel titanium alloys, and/or stainless steel alloys. Ceramic materials such as aluminum oxide or alumina, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various components comprising the prosthetic device 30 may be formed of different materials thus permitting metal on metal, metal on ceramic, metal on polymer, ceramic on ceramic, ceramic on polymer, or polymer on polymer constructions.

In any one of the described embodiments, the bone contacting surfaces of the prosthetic device including contact surfaces, keels, and/or any bridge surfaces may include features or coatings which enhance the fixation of the implanted prosthesis. For example, the surfaces may be roughened such as by chemical etching, bead-blasting, sanding, grinding, serrating, and/or diamond-cutting. All or a portion of the bone contacting surfaces of the prosthetic device may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

The prosthetic device may be installed between adjacent vertebrae as described herein. The prosthetic device may be implanted into a patient using a posterior transforaminal approach similar to the known TLIF (transforaminal lumbar interbody fusion) or PLIF (posterior lumbar interbody fusion) procedures. PLIF style approaches are generally more medial and rely on more retraction of the traversing root and dura to access the vertebral disc space. The space between these structures is known as Kambin's triangle. TLIF approaches are typically more oblique, requiring less retraction of the exiting root, and less epidural bleeding with less retraction of the traversing structures. It is also possible to access the intervertebral space using a far lateral approach, above the position of the exiting nerve root and outside of Kambin's triangle. In some instances, it may be possible to access the intervertebral space via the far lateral without resecting the facets. Furthermore, a direct lateral approach through the psoas is known. This approach avoids the posterior neural elements completely. Embodiments of the current disclosure may adopt any of these common approaches or combinations thereof.

In various embodiments, some or all of the affected disc and surrounding tissue may be removed via the foramina. The superior endplate of the vertebra may be milled, rasped, or otherwise resected to match the profile of the outer contact surface of the lower joint component to normalize stress distributions on the endplate, and/or to provide initial fixation prior to bone ingrowth. The preparation of the endplate of vertebra may result in a flattened surface or in surface contours such as pockets, grooves, or other contours that may match corresponding features on the outer contact surface. The inferior endplate of the vertebra may be similarly prepared to receive the upper joint component to the extent allowed by the exiting nerve root and the dorsal root ganglia. In various embodiments, the natural facet joint and the corresponding articular processes can be rasped and/or prepared to accommodate and/or support an outer surface of the bridge component.

Deployment Tool

Figure 16A:
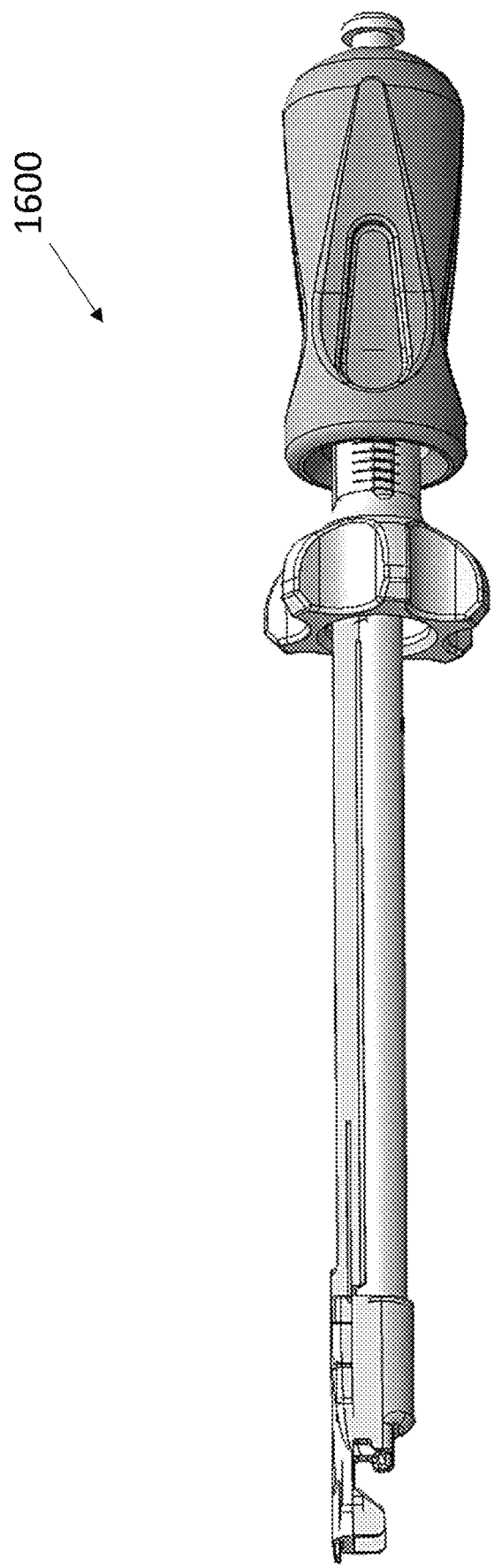
FIGS. 16A and 16B depict perspective and exploded views of an insertion tool for implanting a prosthetic device of the present invention.
Figure 16B:
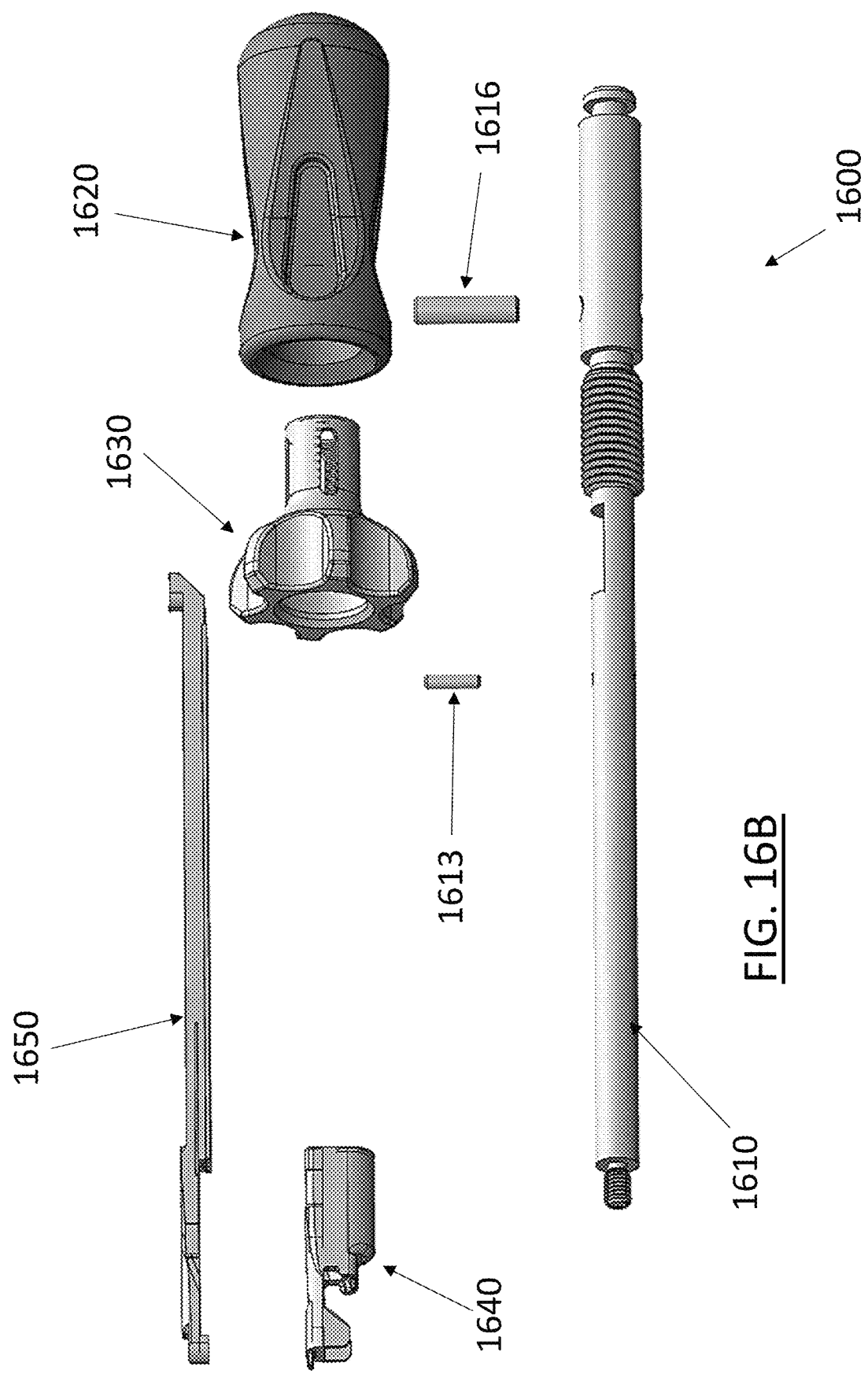
Figure 16C:
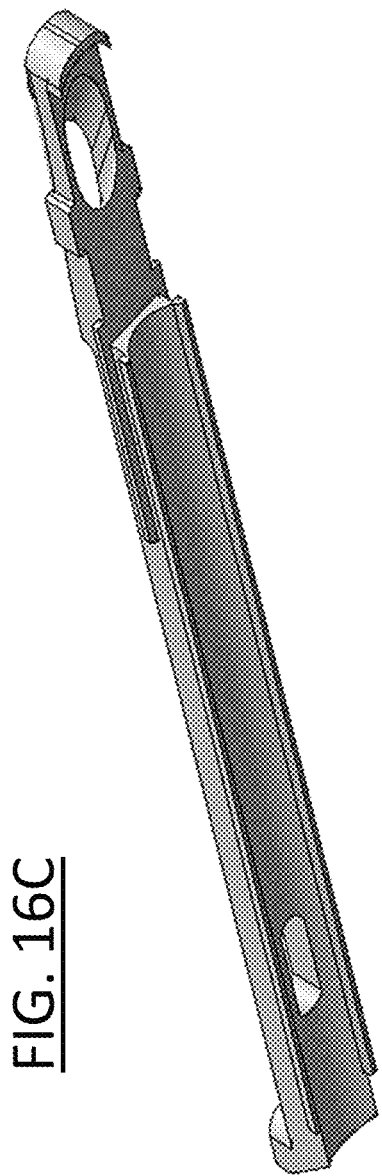
FIGS. 16C and 16D depict various views of a lower component tool.
Figure 16D:
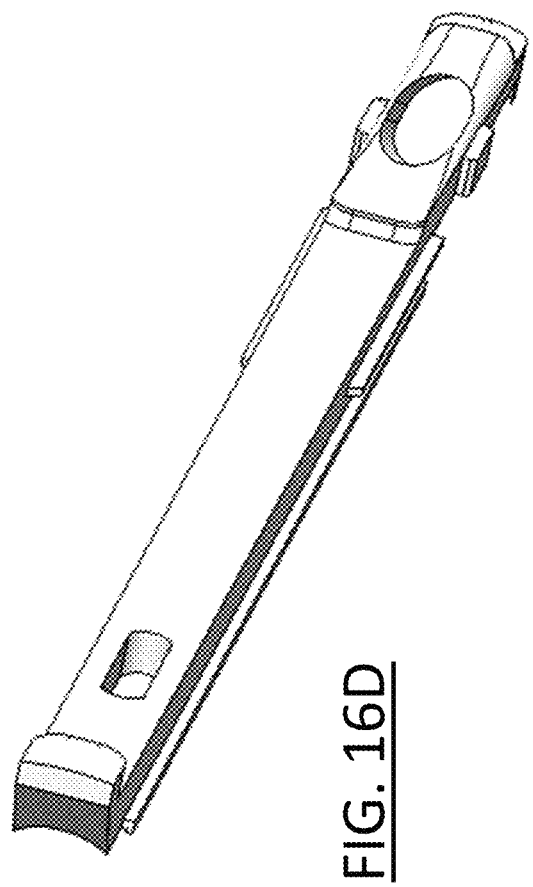
Figure 16E:
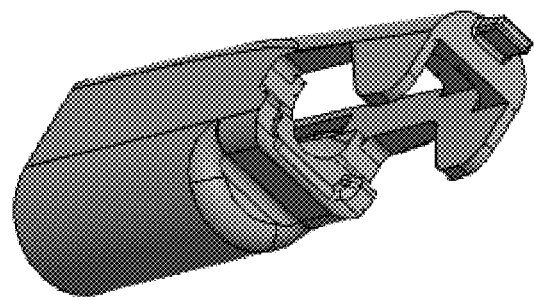
FIGS. 16E and 16F depict various views of an upper component tool.
Figure 16F:
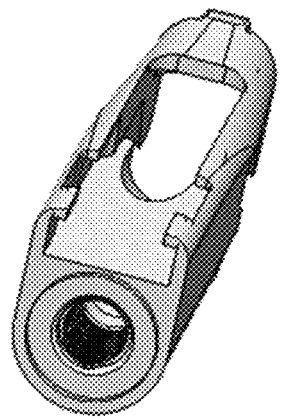
Figure 18A:
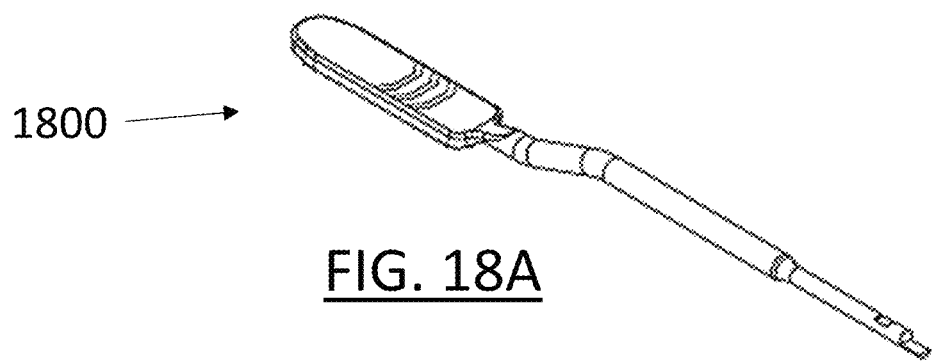
Figure 18B:
Figure 18C:
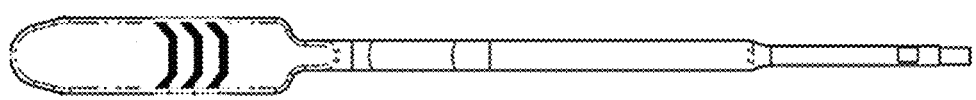
Figure 19A:
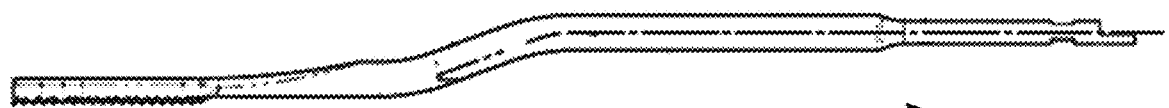
Figure 19B:
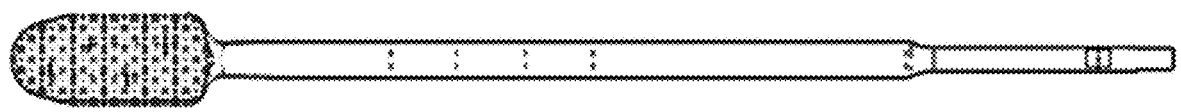
Figure 19C:
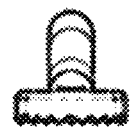
Figure 20A:
Figure 20B:
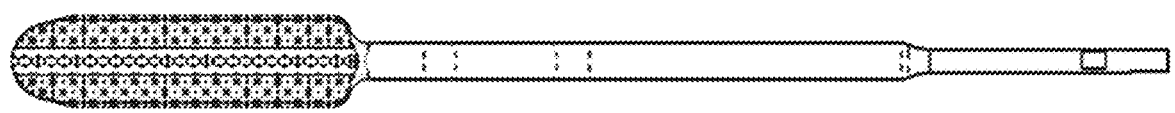
Figure 20C:
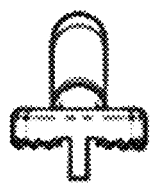

FIGS. 16A and 16B depict a perspective and exploded view of an insertion tool 1600 for implanting a prosthetic device of the present invention. In this embodiment, the tool 1600 includes a central shaft 1610 with a threaded distal tip that is threadably engaged with a lower component tool 1640, and an upper component tool 1650 which slides longitudinally along a pin 1613 in the central shaft 1610 in response to rotation of a rotatable handle 1630. The tool also includes a proximal handle 1620 which is secured to the central shaft 1610 by a pin 1616.

FIGS. 17A and 17B depict partial perspective and exploded views of a distal tip of an insertion tool 1700 with an upper component 1710 and a lower component 1720 secured thereupon. In use, the insertion tool can retain both the upper and lower components for simultaneous insertion in a fully assembled fashion, and further allow a fixation element such as a screw (not shown) to be introduced through an opening in the lower component to secure the device in a desired position and/or orientation. Once the implant is secured to the vertebral body in a desired fashion, the insertion tool 1700 can release the upper and lower components and be removed from the patient.

Exemplary Surgical Procedure

According to at least one embodiment, a first surgical incision for providing access via a bilateral approach is made in the patient's back, and a decompression of the posterior vertebral elements on a first posterior side of the spinal motion unit (i.e., removal of portions of the upper and/or lower facets on the medial side, for example) or other standard bilateral decompression can be accomplished to provide access to the intervertebral disc space. A discectomy can then be accomplished through the access, and a distractor/trial can be placed between the vertebral bodies, with the overlying skin and tissues allowed to relax. A second surgical incision is made to provide access to the opposing (i.e., lateral) side of the spinal motion unit, and then a similar decompression and discectomy can be accomplished through the lateral access.

The surgeon can then rasp, resect and/or otherwise remove portions of the vertebral body, the pedicle and/or other posterior structures of the vertebral body, including portions of the upper endplate of the lower vertebral body, in accordance with the preoperative surgical plan. In various embodiments, the rasp may be operated manually, although the employed of a powered rasp tool may be particularly desirous, especially where significant bony material from the endplate, the cortical rim and/or one or more pedicles is being removed to alter the lordotic angle or other alignment(s) of one or more vertebral bodies.

In various embodiments, various types of flat rasps 1800 or 1900 (see FIGS. 18A through 18C and 19A through 19C) can be utilized to remove and prepare the upper surface of the lower vertebral body and pedicle, and such rasps may be similarly used on the lower endplate of the upper vertebral body, such as to flatten or otherwise prepare the top of the disc space and/or to cut down through pedicles and/or other posterior structures where a significant osteotomy is being performed. Once the upper surface of the lower vertebral body has been prepared using the flat rasp, a keel rasp 2000 (see FIG. 20A) can be utilized to prepare a keel slot or similar feature in the vertebral body and/or pedicle. Once the keel slot of prepared in the lower vertebral body, an indexed rasp 2100 (See FIGS. 21A through 21C) can be used, which desirably includes a non-cutting index 2110 to align with the keel slot to create a top keel and align it with the cut along the pedicle—and the top keel groove can then be formed in the upper vertebral body.

Once one side of the vertebral body and disc space have been prepared in this fashion, a spacer or trial may be placed into the disc space to ensure the vertebral bodies have been properly prepared (if desired)—such as to ensure that a desired angular correction has been established, and/or that a desired tension of the lateral annulus will be achieved once the final implant has been emplaced. If the trial/spacer appears to properly fit, then the trial/spacer can be removed and replaced with the assembled implant. Once the assembled implant is in a desired position, an anchoring screw or other anchoring device can be inserted through the connection component and secured to the lower vertebral body.

In various embodiments, the flat rasp(s) or other surgical tool(s) could be attached to a surgical guidance system, allowing a surgeon to view the predicted and/or actual path of the rasp/tool on the targeted anatomy. Various additional steps of the procedure as outlined could be accomplished using a surgical guidance system, with at least one benefit of surgical guidance potentially reducing radiation exposure to the patient and/or operative room personnel while enhancing the accuracy and/or fidelity of the anatomical preparation by matching the preoperative plan with the intraoperative execution in three dimensions.

In other alternative embodiments, the various steps described herein could be accomplished with the aid of a surgical robot, with or without surgical navigation. In one embodiment, the surgical robot could provide haptic feedback to the surgeon, which might desirably notify the surgeon of approaching soft tissues and/or other surgical boundaries. In another embodiment, the robot could provide rigid limits for surgeon activity (i.e., to prevent cutting into delicate tissues, for example). In a third embodiment, the surgical robot could complete surgical steps autonomously (i.e., with or without surgeon intervention). The employment of surgical robots as outlined could potentially reduce radiation exposure to the patient and/or operative room personnel while enhancing the accuracy and/or fidelity of the anatomical preparation by matching the preoperative plan with the intraoperative execution in three dimensions.

Once one side of the vertebral body has been treated in the previous manner, the same approach can be repeated on the other side of the vertebral body, including trialing and placement of the final implant. One particularly advantageous feature of the present invention is that the disclosed technique allows a surgeon to trial and "balance" the medial and lateral annulus for proper tension/laxity, in a manner similar to balancing of a knee implant. Such balancing, which is not currently possible using existing devices and surgical techniques, can significantly improve the stability and performance of the spinal implant, and can also contribute greatly to device function and durability, as well as significantly reduced patient pain and/or recovery time, leading to increased patient satisfaction with this procedure.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein. What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A surgical method for altering a medial/lateral curvature of a diseased or damaged spine, comprising:
removing at least a portion of a natural facet from at least one of an upper vertebra and an adjacent lower vertebra of the diseased or damaged spine;
removing at least a portion of an intervertebral disc from between the upper vertebra and adjacent lower vertebra to create a disc space, wherein an endplate of the adjacent lower vertebra has a generally planar natural endplate surface;
removing a first wedge of bony material from the endplate of the adjacent lower vertebra to create a first modified vertebral surface which is non-parallel to the generally planar natural endplate surface, at least a first portion of the first modified vertebral surface cutting completely through a posterior cortical bone surface of the endplate and a posterior cortical ring of the adjacent lower vertebra without completely removing an anterior cortical bone surface of the endplate of the adjacent lower vertebra,
removing at least a first portion of a first pedicle of the adjacent lower vertebra to create a first modified pedicle surface which extends along a resected surface of the first pedicle;
inserting a lower portion of a first arthroplasty device at least partially into the disc space, the lower portion of the first arthroplasty device including an upward facing articulation surface, a first lower surface adapted to engage with the first modified vertebral surface and a bridge portion adapted to engage with the first modified pedicle surface; and
attaching the lower portion of the first arthroplasty device to the adjacent lower vertebra with a bone fastener.

2. The surgical method of claim 1, wherein the step of removing a wedge of bony material from the endplate of the adjacent lower vertebra comprises milling at least a portion of the natural endplate of the adjacent lower vertebra.

3. The surgical method of claim 1, wherein the step of removing a wedge of bony material from the endplate of the adjacent lower vertebra comprises resecting at least a portion of the natural endplate of the adjacent lower vertebra.

4. The surgical method of claim 1, wherein the step of removing a wedge of bony material from the endplate of the adjacent lower vertebra comprises rasping at least a portion of the natural endplate of the adjacent lower vertebra.

5. The surgical method of claim 1, wherein the steps of removing a wedge of bony material from the endplate of the adjacent lower vertebra and removing at least a portion of a pedicle of the adjacent lower vertebra are performed concurrently.

6. The surgical method of claim 1, wherein the first modified vertebral surface and the first modified pedicle surface are parallel.

7. The surgical method of claim 1, wherein the first modified vertebral surface and the first modified pedicle surface are coplanar.

8. The surgical method of claim 1, wherein the first modified vertebral surface and the generally planar natural endplate surface differ by up to 10 degrees.

9. The surgical method of claim 1, wherein the first modified vertebral surface and the generally planar natural endplate surface differ by up to 15 degrees.

10. The surgical method of claim 1, wherein the first modified vertebral surface and the generally planar natural endplate surface differ by up to 20 degrees.

11. The surgical method of claim 1, wherein the first modified vertebral surface and the generally planar natural endplate surface differ by up to 25 degrees.

12. The surgical method of claim 1, wherein the first modified vertebral surface and the generally planar natural endplate surface differ by up to 30 degrees.

13. The surgical method of claim 1, further comprising inserting an upper portion of the first arthroplasty device at least partially into the disc space, the upper portion of the first arthroplasty device including a downwardly facing articulation surface which articulates with the upward facing articulation surface of the lower portion to allow the upper vertebra and adjacent lower vertebra to articulate relative to each other, the upper portion further including a first upper surface adapted to engage with the upper vertebra.

14. The surgical method of claim 1, wherein the upper and lower portions of the first arthroplasty device are concurrently inserted at least partially into the disc space.

15. A surgical method for altering a lateral curvature of a spine, comprising:
   removing at least a portion of a natural facet from a lower vertebra of the spine, an upper endplate of the lower vertebra having a presurgical endplate plane;
   removing at least a portion of an intervertebral disc from between the lower vertebra and an adjacent upper vertebra to create a disc space;
   removing bony material from the upper endplate of the lower vertebra to create a modified vertebral body surface which is angled relative to the presurgical endplate plane, at least a portion of the modified vertebral body surface cutting completely through the cortical bone of the endplate to expose a cancellous bone interior of the lower vertebra;
   removing at least a first portion of a first pedicle of the lower vertebra to create a resected pedicle surface which extends along at least a portion of the first pedicle;
   inserting a lower portion of a first arthroplasty device at least partially into the disc space, the lower portion of the first arthroplasty device including an upward facing articulation surface, an anterior lower surface adapted to engage with the modified vertebral body surface and a posterior bridge portion adapted to engage with the resected pedicle surface; and
   attaching the lower portion of the first arthroplasty device to the adjacent lower vertebra with a bone fastener.

16. The surgical method of claim 15, wherein the steps of removing bony material from the upper endplate of the lower vertebra and removing at least a first portion of a first pedicle of the lower vertebra are accomplished concurrently using a powered rasp.

17. The surgical method of claim 15, wherein the modified vertebral body surface and the presurgical endplate plane differ by up to 30 degrees.

18. The surgical method of claim 15, wherein the anterior lower surface and the posterior bridge portion of the lower portion of the first arthroplasty device are coplanar.

19. The surgical method of claim 15, wherein an anterior portion of the modified vertebral body surface comprises a cortical bone of the upper endplate.

20. The surgical method of claim 15, wherein the bone fastener extends through the resected pedicle surface.

* * * * *